United States Patent [19]

Specht et al.

[11] Patent Number: 4,805,123

[45] Date of Patent: Feb. 14, 1989

[54] AUTOMATIC PHOTOMASK AND RETICLE INSPECTION METHOD AND APPARATUS INCLUDING IMPROVED DEFECT DETECTOR AND ALIGNMENT SUB-SYSTEMS

[75] Inventors: Donald F. Specht, Los Altos; Tim S. Wihl, San Jose; Scott A. Young, Scotts Valley; James J. Hager, Jr., San Jose; Matthew B. Lutzker, Menlo Park, all of Calif.

[73] Assignee: KLA Instruments Corporation, Santa Clara, Calif.

[21] Appl. No.: 885,197

[22] Filed: Jul. 14, 1986

[51] Int. Cl.$^4$ .......................... G06K 9/68; G06K 9/38
[52] U.S. Cl. ................................... 364/559; 356/394;
 382/8; 382/34; 382/48; 358/105
[58] Field of Search ................ 364/518, 559; 356/394;
 382/8, 34, 48, 45, 46; 358/105, 106, 160, 166

[56] References Cited

U.S. PATENT DOCUMENTS

| | | | |
|---|---|---|---|
| 3,573,789 | 4/1971 | Sharp | 347/728 |
| 4,110,737 | 8/1978 | Fahey | 382/44 |
| 4,129,860 | 12/1978 | Yonezawa et al. | 340/728 |
| 4,136,332 | 1/1979 | Kadota et al. | 382/34 |
| 4,153,897 | 5/1979 | Yasuda et al. | 382/34 |
| 4,200,861 | 4/1980 | Hubach et al. | 382/48 |
| 4,437,121 | 3/1984 | Taylor et al. | 382/46 |
| 4,441,205 | 4/1984 | Berhin et al. | 382/34 |
| 4,448,532 | 5/1984 | Joseph et al. | 356/394 |
| 4,611,232 | 9/1986 | Searby | 358/160 |
| 4,614,430 | 9/1986 | Hara et al. | 382/8 |
| 4,631,750 | 12/1986 | Gabriel et al. | 382/44 |
| 4,644,584 | 2/1987 | Nagashima et al. | 382/48 |
| 4,651,341 | 3/1987 | Nakashima et al. | 382/34 |
| 4,669,123 | 5/1987 | Kobayashi et al. | 382/8 |
| 4,680,630 | 7/1987 | Field | 382/46 |
| 4,693,608 | 9/1987 | Kitagawa et al. | 356/394 |
| 4,701,859 | 10/1987 | Matsuyama et al. | 382/8 X |

FOREIGN PATENT DOCUMENTS 3340705 5/1984 Fed. Rep. of Germany .

*Primary Examiner*—Felix D. Gruber
*Assistant Examiner*—Joseph L. Dixon
*Attorney, Agent, or Firm*—Rosenblum, Parish & Bacigalpi

[57] ABSTRACT

A photomask and reticle inspection method and apparatus wherein a selected surface area of an object is inspected and a first stream of data having signal values representing the image content of each pixel thereof is generated, a second stream of data having signal values representing the intended image content of each pixel of the first stream of data is generated, corresponding portions of the first and second streams of data are stored in memory, any misalignment between the stored portions of the first and second streams of data is detected, the misaligned first and second portions of data are then aligned using shifts of an integral number of pixels and/or subpixel interpolation to correct the detected misalignment therebetween, corresponding subportions of the stored and aligned first and second portions of data are then compared to detect difference therebetween, and upon detecting a difference exceeding a predetermined threshold, the presence of a defect at a particular pixel location on the inspected object is indicated.

52 Claims, 13 Drawing Sheets

BILINEAR INTERPOLATION EXAMPLE

X INTERPOLATION = X SHIFT OF -2 TO +1 15/16 PIXEL
RESOLUTION = 1/16 PIXEL

Y INTERPOLATION = Y SHIFT OF -1 TO +1 15/16 PIXEL
RESOLUTION = 1/16 PIXEL $E = A(3/4) + B(1/4)$
$F = C(7/8) + D(1/8)$
$G = E(15/16) + F(1/16)$

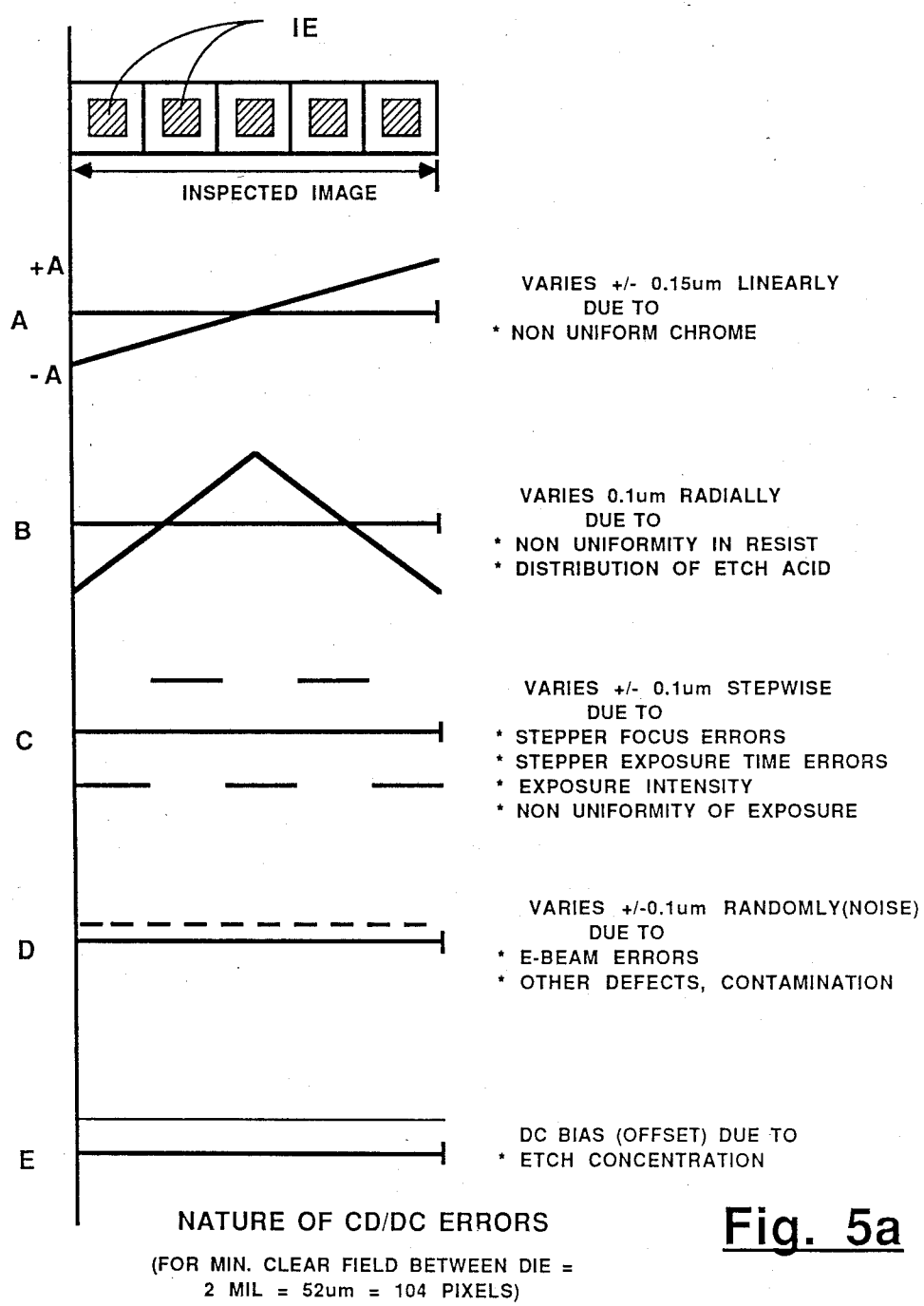

AUTOMATIC PHOTOMASK AND RETICLE INSPECTION METHOD AND APPARATUS INCLUDING IMPROVED DEFECT DETECTOR AND ALIGNMENT SUB-SYSTEMS

BACKGROUND OF THE INVENTION

1. Field of the Invention

The present invention relates generally to microscopic inspection methods and apparatus, and more particularly to an improved photomask and reticle inspection method and apparatus capable of automatically detecting and identifying extremely small defects in a photomask, or the like, by comparing portions of the inspected photomask to either other portions of the same mask or to data corresponding to similar portions stored in a pre-existing database.

2. Description of the Prior Art

It has long been known that defects in photomasks and other objects including arrays of repeated geometrical designs can be detected by comparing one portion of the array to a corresponding portion of another part of the array. For example, in the devices disclosed in the U.S. Pat. Nos. 4,247,203 and 4,347,001, to Keneth Levy et al, photomask defects are optically detected by simultaneously scanning two portions of a narrow strip of the same photomask which if without defect would be identical. Any differences between the two detections indicate that there is a possible defect in one of the mask portions, and such defect can be specifically located and identified. Although such devices have long provided reliable detection of mask defects, it has been found that the detection system itself may generate spurious signals which show up in the output as defects when no actual defect is present. These "false defects" may result from such things as slight differences in geometries of the inspected mask portion, differences in focusing of the images onto the detectors, differences in illumination, vibrations of the system, misalignment of the inspected image and the reference image, intermittent memory bits and other similar problems.

An effort to provide a solution to the false defect problem is disclosed in U.S. Pat. No. 4,448,532 issued to David A. Joseph et al. In the disclosed apparatus, photomask defects are likewise optically detected by simultaneously scanning two portions of a narrow strip of the same photomask. However, "false defects" are avoided by rescanning each scan line if a defect is recorded, comparing the outputs thereof and discarding those detected defects which are not common to the two scans. More specifically, if no defect is found on the first scan then there is no reason to re-scan the line. But if defects are detected, the same line is re-scanned in the reverse and comparing the results of the two scans are compared and non-matching defect indications are discarded. Only the common defects are identified as real defects.

As the technology improved, it was found that prior inspection systems had relatively poor detection efficiency for defects located near corners. One attempt to overcome such in-efficiency was to use some kind template matching technique. However, there almost always existed cases involving unusual quantization in which errors occurring at or near image corners were missed.

Still another attempt to improve the detection efficiency and accuracy of photomask inspection systems is disclosed in the copending U.S. patent application of Kenneth Levy et al, Ser. No. 492,658, filed May 9, 1983 now U.S. Pat. No. 4,579,455. In accordance with this approach an area subtraction technique is used identify defects as differences between otherwise duplicate die patterns in a photomask. Two square window matrices of seven rows and seven columns of adjacent pixels are defined for corresponding areas of two die patterns of a single photomask (or a die pattern of a photomask and corresponding data taken from a pre-recorded database). The center $3 \times 3$ matrix of each window matrix is defined as a comparison matrix with each matrix having twenty-five unique subsets of $3 \times 3$ adjacent pixels within its boundaries; one in the center plus twenty four others that are offset by one or two pixels from the center in one or both directions. An error value is then calculated for each subset of each window matrix by summing the squares of the differences between each of the nine pixels values of each subset and the corresponding pixel values of the opposite comparison matrix. If there is no defect, and misalignment between the two representations is less than approximately two pixels in magnitude, at least one error value will be less than a threshold error value. If none of the twenty-five error values relating to one comparison matrix are less than the threshold value, a defect is assumed to be located within the comparison matrix or within the opposite window matrix. The magnitude of the threshold error is then automatically varied according to the number of edges within the window matrices to compensate for errors caused by different quantization of edges.

Among the advantages of this approach is that it dynamically and accurately inspects the photomask by identifying defects without requiring two perfectly aligned pixel representations. Furthermore, the sensitivity level of the defect detection circuit is made adaptive so as to improve actual defect detection while reducing false defect detection.

Although the foregoing devices have provided reliable detection of mask defects and have substantially reduced the false defect problem, it has remained desirable to improve the detection device even further to provide electronic correction for critical dimension variation, data collection variation, skew variation, magnification variation, and alignment variation. It has also remained desirable to provide improved sensitivity to defects regardless of the surrounding geometry, and in particular, to defects occurring near corners.

Each of the above mentioned patents and the patent application are assigned to the assignee of the present invention and the entire disclosure of each is expressly incorporated by reference into this application for teaching purposes.

SUMMARY OF THE PRESENT INVENTION

It is a primary objective of the present invention to provide an improved defect detection method and apparatus having improved immunity to variations in alignment, optical deficiencies and signal processing induced errors.

Another object of the present invention is to provide a method and apparatus of the type described which is particularly suited for use in detecting defects in photomasks, reticles, semiconductor wafers and printed circuit boards and the like.

Another objective of the present invention is to provide a method and apparatus of the type described in which means is provided to compensate for critical dimension variation.

Still another objective of the present invention is to provide a method and apparatus of the type described in which means are provided for compensating for skew and magnification variations.

Another objective of the present invention is to provide a method and apparatus of the type described which achieves improved thoroughness, i.e., sensitivity to defects regardless of surrounding geometry, by precision alignment and correction for critical dimension variation and skew and magnification variation so that detection by area subtraction techniques can be utilized with a high level of accuracy and without excessive false defects.

Yet another objective of the present invention is to provide an improved method and apparatus of the type described having means for providing electronic corrections for skew and magnification variation, critical dimension variation, and a new approach to defect detection.

A further objective of the present invention is to provide a method an apparatus of the type described in which resampling of the digitized data on the left and or right side is accomplished so that data from the two sides can be shifted in sub-pixel increments.

A still further objective of the present invention is to provide a method and apparatus of the type described in which an alignment subsystem computes on the fly at full data rate the sum of squared differences between two images digitized to many shades of gray and uses such information to electronically align the inspected and reference images.

An additional objective of the present invention is to provide a method and apparatus of the type described, that includes a detector, the operation of which is based upon measuring the sum of squared differences between each pixel of an n×n sub-array of data from one optical objective to that of another optical objective, or to the corresponding data of a data base.

Another objective of the present invention is to provide a method and apparatus of the type described wherein gate arrays are used to make mechanization of the detector and alignment algorithms economically feasible.

Briefly, one aspect of the present invention is embodied in a method of detecting defects in objects such as photomasks and the like, comprising inspecting a selected surface area of an object and generating a first stream of data having signal values representing the image content of each pixel thereof, generating a second stream of data having signal values representing the intended image content of each pixel of the first stream of data, storing corresponding portions of the first and second streams of data in memory, detecting any misalignment between the stored portions of the first and second streams of data, aligning the stored first and second portions of data to correct any detected misalignment therebetween using shifts of an integral number of pixels and/or subpixel interpolation, and comparing corresponding subportions of the stored and aligned first and second portions of data to detect differences therebetween, and upon detecting a difference, indicating the presence of a defect at a particular pixel location on the inspected object. In another embodiment the present invention includes apparatus for implementing the above method.

An important advantage of the present invention is that through the use of the disclosed resampling technique many of the problems associated with the sampling grid hitting the corresponding geometries in the two data streams out-of-phase with one another is avoided.

Another advantage of the present invention is that the alignment system is able to maintain precise alignment with smaller linewidths than has heretofore been possible.

These and other objects and advantages of the present invention will no doubt become apparent to those skilled in the art after having read the following detailed description of preferred embodiments which are illustrated in the several figures of the drawing.

IN THE DRAWING

FIG. 5a is a diagram illustrating the nature of the errors corrected by the CD corrector subsystem;

DETAILED DESCRIPTION OF THE PREFERRED EMBODIMENTS

Method and Apparatus Generally

Figure 1:
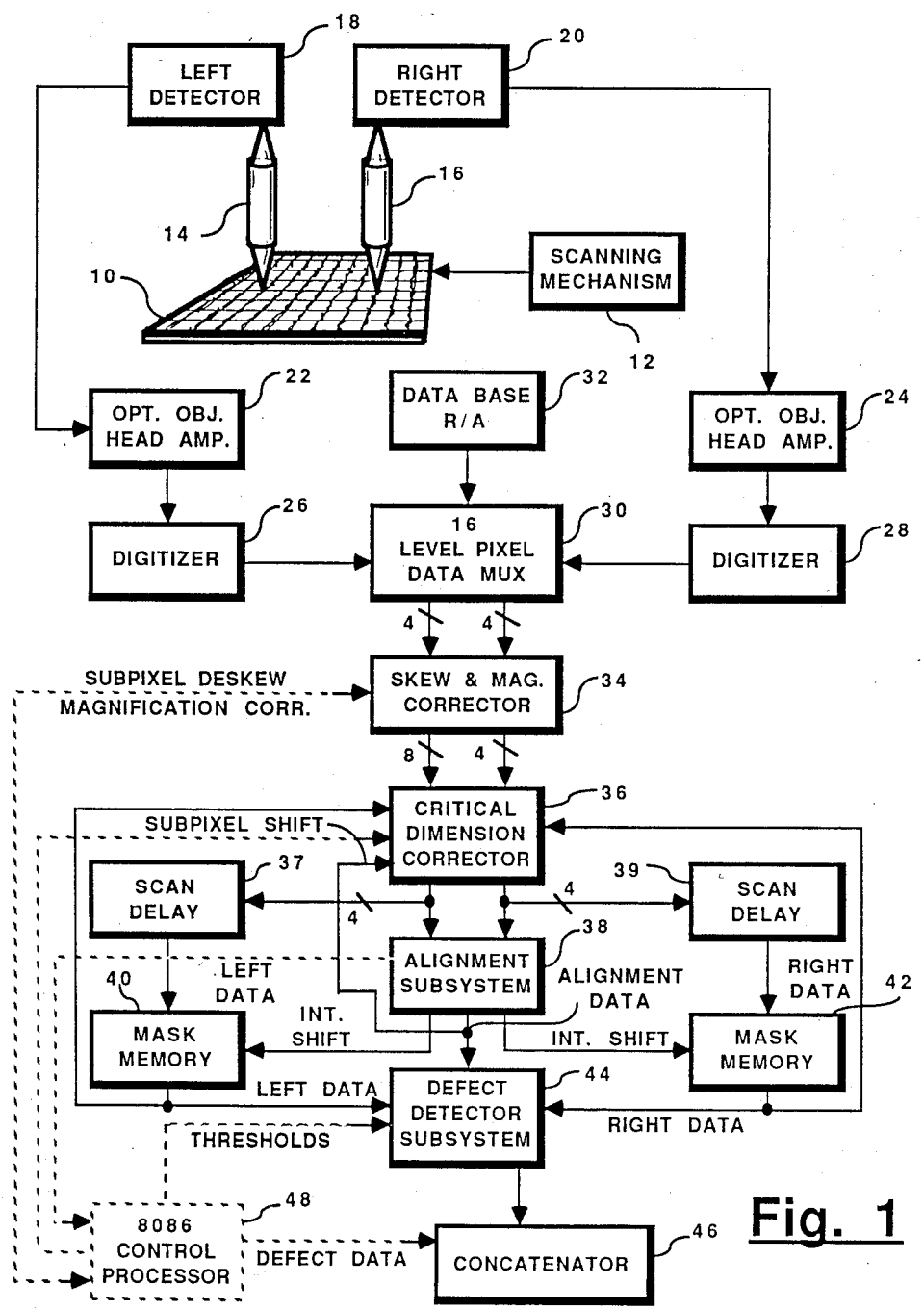
FIG. 1 is a block diagram illustrating an improved photomask inspection system in accordance with the present invention.

Referring now to FIG. 1 of the drawing, a simplified block diagram of a photomask inspection apparatus in accordance with the present invention is depicted. As illustrated, a photomask 10 is placed upon a movable carriage (not shown) forming a part of the scanning mechanism 12. Under control of the system processor, the scanning mechanism 12 causes the photomask 10 to be moved in a predetermined manner relative to a pair of optical detection heads 14 and 16 which are positioned at a separation relative to each other such that the optical axis of each intersects an identical portion of each die contained in the mask 10. As is fully described in the above referenced prior art patents mask 10 is moved in a predetermined manner relative to the heads 14 and 16 to define a predetermined scan pattern across the surface thereof. As the scan is accomplished, light from the mask 10 is transmitted through the heads 14 and 16 onto left and right detectors 18 and 20 respectively, which in the preferred embodiment include 1×n arrays of photo diodes that are electronically scanned to develop data corresponding to each pixel of the mask 10.

Figure 2:
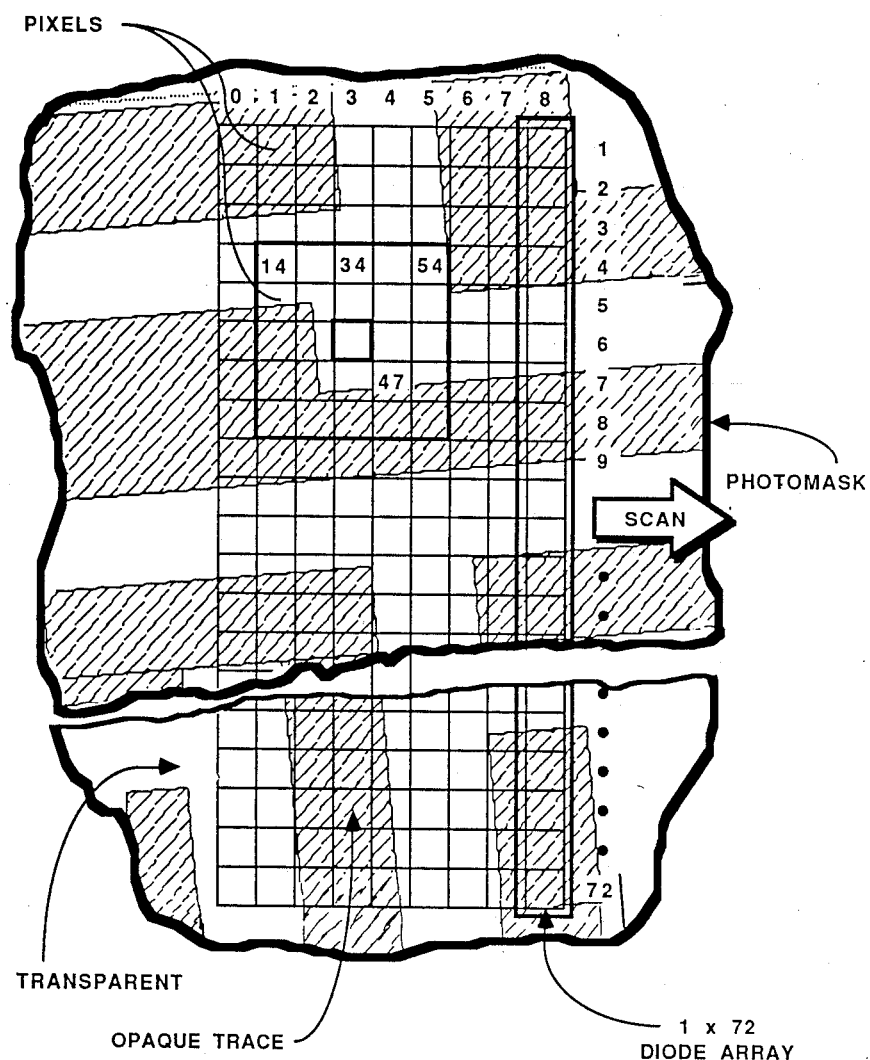
FIG. 2 is a pictorial diagram illustrating the way in which a photomask is scanned in accordance with the present invention.

By way of illustration, reference is made to FIG. 2 of the drawing which shows a segment of a photomask with a 1×n array superimposed thereon to illustrate scan direction and seven previous columns of detected pixels.

The outputs of detectors 18 and 20 are fed into optical objective head amps 22 and 24 respectively, where the signals are amplified and preconditioned, and then transmitted into digitizers 26 and 28 which develop multi-level pixel data (16 level in the preferred embodiment) for input to the data mux 30. Alternatively, prestored pixel data may also be input to data mux 30 from a database 32 for comparison to one of the scan inputs. In the illustrated embodiment, the input to and output from data mux 30 are in the form of 16 bits in parallel from each data source such that information from 4 contiguous pixels (4 bits per pixel) is communicated.

Data mux 30 will input either data from digitizer 26 and 28 or data from one of the digitizers (normally the left detector stream) and the database 32 into the skew and magnification (S&M) corrector subsystem 34 which corrects for skew (image rotation) and magnification (optical distortion) differences between the left and right objectives 14 and 16, or between the database 32 and the selected optical objective, as will be pointed out in more detail below. Subsystem 34 is comprised of scan storage for four previous scans of data as well as the current scan for the objective to be corrected. For example, the pixel data corresponding to the previously scanned columns 4-7 in FIG. 2, where column 8 is considered to be the current column. It is further comprised of subpixel correction circuitry to correct the residual skew, magnification, and distortion differences between the two data streams output to less than one sixteenth of a pixel. It will be noted that the left and right data streams out of subsystem 34 are 8 bits and 4 bits wide respectively. Eight bits of data are used on the left side in the preferred embodiment in order to avoid truncation errors at this point in the system. The cost penalty of carrying 8 bits into the CD corrector is low, but the cost penalty of carrying additional bits ou of the CD corrector through the scan delays and mask memories is high. Therefore, the data is truncated to 4 bits/pixel of the output of the CD corrector 36.

Data from subsystem 34 is input to a critical dimension and DC offset correction subsystem 36 which compensates for critical dimension variation from left to right objective, or from objective to database, by moving the digitizing thresholds up and down differentially. Critical dimension variations are typically variations in linewidths caused by process variations. The subsystem makes use of the unavoidable fact that the basic geometry is convolved with the Airy function which represents the optical point spread function. By moving the digitizing thresholds up and down, the traces on the mask 10 can be effectively widened or made more narrow. The same effect can be obtained by a digital remapping of the grey levels from the digitizer.

As further explained below, the CD/DC correction subsystem 36 is comprised of remapping PROMs plus detection circuitry which measures the difference in white to black ratio on both sides and selects a mapping function to provide appropriate compensation. The sign of the difference determines the direction of change. The amount of the change is determined by dividing the difference area by the number of edge pixels involved. Subsystem 36 also corrects for one shade of grey DC offset from the digitizors 26 and 28. When the mode of a histogram of grey values indicates that the end values of the digitizer range are "1" or "E" instead of "0" and "F", the 1's are mapped to 0 and the E's are mapped to F.

The output of subsystem 36 is input to an alignment subsystem 38 which performs the function of determining dynamically the registration error between the left and right images. It is comprised of an image data buffer, alignment error detectors and alignment processors. The alignment error detector finds the sum of squared differences (SSD) over a window which is 480 pixels high (Y) and five pixels wide (X) for relative displacements of 0 and +/−1, 2, 3, 4, 5, 6, and 7 pixels in both dimensions. This results in a 15×15 map of SSD measurements.

Subsystem 38 first combines pairs of consecutively sampled SSD maps into similar maps which are based on 10 scans of data and which are updated after every 5 scans of data. From the 10 scan map, subsystem 38 finds the minimum value in the map and then interpolates between such value and its neighbors to estimate the optimal displacement with an accuracy of +/−0.25 pixel and a precision of +/−0.07 pixel.

The interpolation algorithm is based upon the assumption that the SSD surface is locally parabolic in the region of the minimum value. Five cases are treated: In general, if the geometry in the correlation window contains edges in more than one orientation, the sum of squares surface is assumed to be locally a three dimensional paraboloid with its major axis in any orientation. If the geometry in the correlation window consist of traces in only one orientation, the sum of squares surface is assumed to be a ridge with a parabolic cross section. This case is further subdivided into the cases of vertical ridge, horizontal ridge, and ridge of arbitrary orientation. The remaining case is that in which there is no geometry in the correlation window, in which case the SSD surface is flat or almost flat. The interpolation algorithm determines which of the three cases exists and treats them as follows:

1. If the map is flat or almost flat, it makes no change to the last values output for X and Y misalignment.

2. If the geometry in the correlation window contains edges in more than one orientation, then the alignment processor finds the minimum value of the SSD map and restricts further computation to the 5×5 subarray of SSD values centered on that minimum. By using first and second differences and standard mathematical techniques, it computes the location of the bottom of the paraboloid. The coordinates of the bottom are the X and Y shifts outputs of the alignment subsystem.

3. For the three ridge cases, the search is restricted to finding the bottom of a parabola instead of a paraboloid. Note that the ridge in the SSD map is a line of points which are all approximately the same (the minimum). In order to avoid jumping from one minimum point to another based on random noise, the result in these cases is further constrained such that the change in shift outputs is in a direction perpendicular to the geometry in the correlation window.

The result of the interpolation computation is the misregistration in X and Y in integral and fractional pixels (down to 1/15th or 1/16th pixel depending on the detector requirement). Before passing this data downstream to the mask memories and the detectors, the data stream is low-pass filtered using firmware in the alignment processor. A system frequency response of about 200 Hz allows the alignment system to follow and correct for mechanical vibrations. Lower values of bandwidth effectively increase the size of the correlation window. This increases alignment accuracy in cases where mechanical vibration frequencies can be reduced.

The scan delay units 37 and 39 delay the image data 3 to 32 scans to compensate for the computation delay through the alignment system. The amount of delay is programmable. The programmable scan delays 37 and 39 respectively feed left pixel data into a mask memory 40 and right pixel data into a mask memory 42.

Subsystem 44 is comprised of two separate detectors; one intended for use in the die-to-database mode and one intended for use in the die-to-die mode of operation. However, either detector can be used for either mode of operation. The die-to-database detector portion uses a minimum squared error criterion with a 5×5 pixel window, and steps −2/3, −1/3, 0, +1/3, and +2/3 pixels in both dimensions to find the best shift of 25 possible shifts. A threshold is applied to the minimum squared error to determine whether or not a defect exists. Although the mask memory shifts integral pixels as required by the alignment processor, the remainder of the shift from 0 to +14/15 pixel is performed in the detector in steps of 1/15 pixel. The alignment processor will cause the mask memory to shift such that the subpixel remainder is always positive.

The die-to-die detector portion of subsystem 44 is based on simply subtracting a 2×2 pixel window on one side from a 2×2 pixel window on the other side. After shifting one side by the fractional shift from the alignment system, the four pixels are added together, subtracted from the sum of the four from the other side, and then the absolute value of the difference is compared with the threshold. The detected defect data is then output to a concatenator 46.

In addition to the above described components, the system includes an 8086 control processor 48 which controls operation of the various subsystems.

Skew and Magnification Corrector

Figure 3:
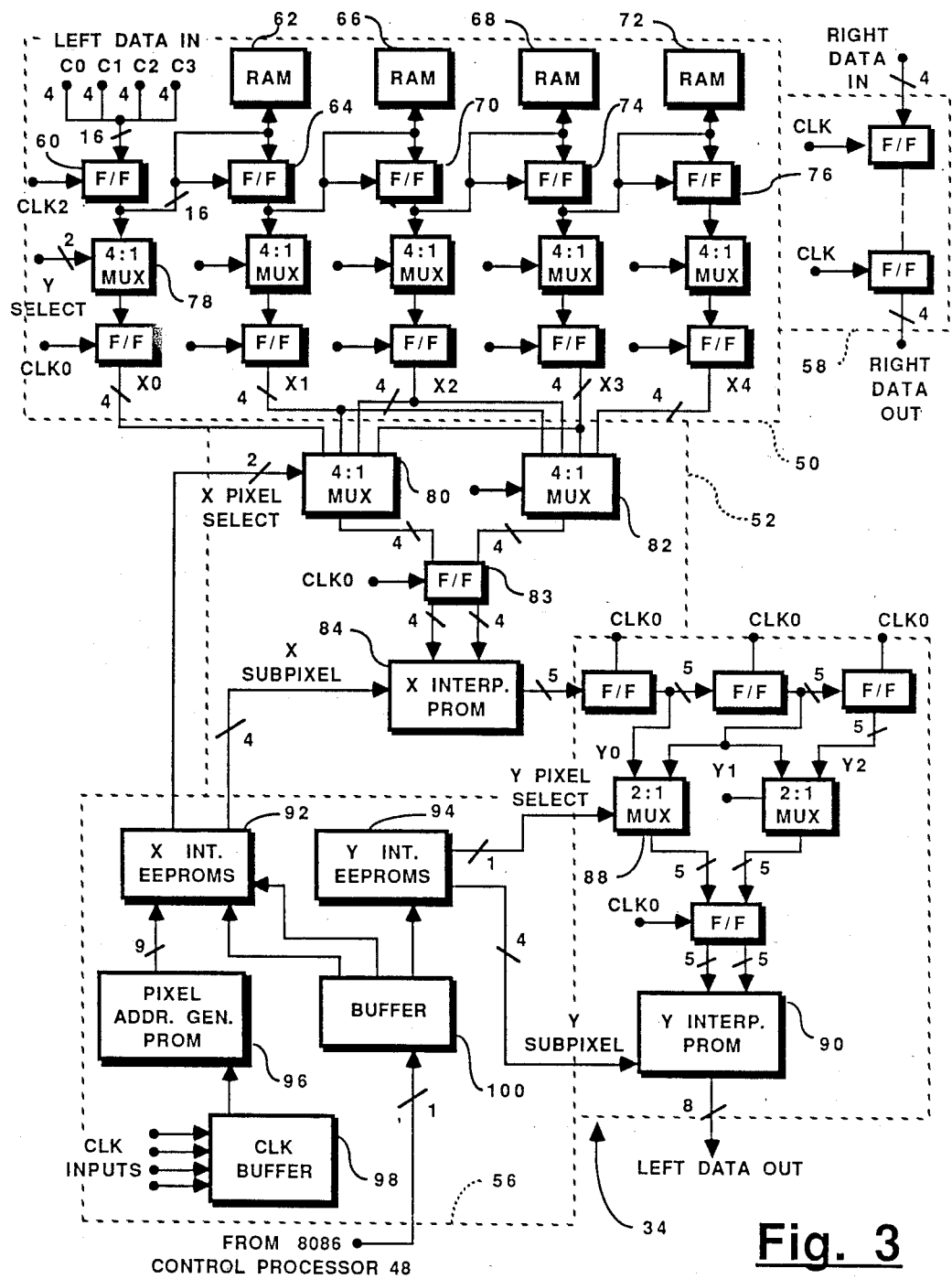
FIG. 3 is a block diagram illustrating the skew and magnification corrector subsystem shown in FIG. 1.

Referring now to FIG. 3 of the drawing, further details of the skew and magnification corrector subsystem 34 will be described. As indicated, subsystem 34 may be subdivided into five component subcircuits; namely, a scan storage subcircuit 50, an X interpolation subcircuit 52, a Y interpolation subcircuit 54, and a control subcircuit 56, all of which form the left side data path. Subsystem 34 also includes a pipeline adjust subcircuit 58 which forms the right side data path. As indicated, 16 level pixel data corresponding to 4 pixels is input in parallel at C0, C1, C2, and C3, and the 16 bits of data are clocked through a register or flip-flop 60 into a first RAM 62 which stores 1 scan of data. On the next clock, a second scan of data is input into RAM 62, and the first scan data is input via a flip-flop 64 into a second RAM 66.

During the next two clocks the first set of scan data is input to RAM 68 via flip-flop 70 and then into RAM 72 via flip-flop 74. It will thus be appreciated that at this point the last four scans of data be stored in RAMs 62, 66, 68, and 72, and the current scan will appear at the input to flip-flop 60. The five flip-flops 60, 64, 70, 74, and 76 thus form five 16 bit wide data streams in parallel. These data streams are then converted by means of 4:1 multiplexors 78 from pixel parallel to pixel serial format thus forming five four-bit data streams X0–X4. Datastreams X0–X3 are input to a first 4:1 mux 80, and data steams X1–X4 are input to a second 4:1 mux 82. The two multiplexors 80 and 82 select an adjacent pair of bit streams, depending on what the subsystem decides is the proper correction, and inputs them via register 83 to the X interpolation PROM 84.

If no correction is required, the data stream X2 merely passes through the multiplexors 80 and 82. However, any adjacent pair of pixel streams may be selected for input into the X interpolation PROM 84. The X interpolated data is then fed through a series of registers 86 which develop data streams Y0, Y1 and Y2. Two of the three data streams are then selected by the 2:1 multiplexers 88 for interpolation in Y to provide for the multiplication correction. The Y interpolation prom 90 then creates one pixel data from the two inputs, with such data being truncated at 8 bits.

Figure 4:
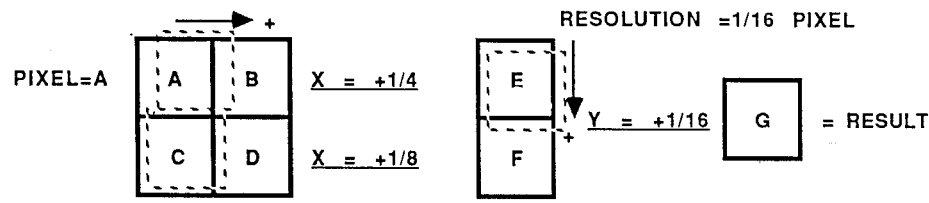
FIG. 4 is a diagram illustrating an example of bilinear interpolation as accomplished in the skew and magnification corrector subsystem of FIG. 3.

In FIG. 4 a graphical example of the manipulation of the left data is given. In this example it is presumed that the X shift that is required is +¼ of a pixel from A to B and that the next pair of pixels immediately below is to be shifted in X by ⅛ of a pixel. The X interpolation will work first on the A-B pair to generate the pixel E and then next on the C-D pair to generate the pixel F. It will thus be appreciated that the value of pixel E is equal to ¾ the value of pixel A plus ¼ the value of pixel B. Similarly, the value of pixel F is 7/8 times the value of pixel C plus ⅛ times the value of pixel D. This is linear interpolation in X. Then, as depicted, a downward shift in Y of 1/16 of a pixel is required, and as a consequence, the pixel G is generated as a linear combination of E and F. Thus, the value of pixel G is 15/16 of pixel E plus 1/16 of pixel F. The X and Y interpolation is explained mathematically by the three equations immediately beneath the diagrams.

Returning again to FIG. 3 of the drawing, the control circuit for corrector 34, is shown to include a pair of EEPROMs 92 and 94 which respectively control the X interpolation operation and the Y interpolation operation. In addition, the circuitry includes a pixel address generator PROM 96, a clock buffer 98, and a buffer 100. Both of the EEPROMs 92 and 94 receive a slow speed load of interpolation data from the system controller 48 (FIG. 1) during calibration. During the actual scanning operation the 9 bits used are 8 bits generated by the pixel PROM address generator 96, (a counter) plus 1 bit which comes from the control processor 48 and indicates the present stage direction. The counter indicates to the PROMS which corrections are needed. Instantaneously, 6 bits of interpolation information is provided by the EPROMs 92 to the X interpolation sub-circuit 52, and 5 bits of information are provided to the Y interpolation sub-circuit 54 as the diode arrays contained in the detectors 18 and 20 (FIG. 1) are scanned from top to bottom. When the corrections downloaded into EEPROMS 92 and 94 are based on an appropriate calibration procedure, the subsystem can correct for rotation of the diode arrays and differences in magnification and distortion of the optical systems.

While the left side data is being processed as described above, the right side data is merely passing through various stages of delay in sub-circuit 58 so as to emerge therefrom at appropriate times corresponding to the output of left data from sub-circuit 54.

Although the above discussion of the skew and magnification corrector describes the details of one particular implementation, several improvements are possible and indeed may be preferable. First, the X and Y interpolation PROMS 84 and 90 might be look-up tables not limited to linear combinations of the input pixels. One nonlinear approach of value for inspecting photomasks and reticles is S-curve interpolation which uses the a-priori knowledge that transitions from opaque to clear portions of the mask follow a characteristic S shaped curve. From the information that the two input pixels are exactly 1 pixel apart, the prototypical S-curve can be expanded or contracted to conform. The interpolated data can be found as the ordinate corresponding to the abscissa value which is the desired subpixel fraction from one to the other of the input pixels.

Secondly, FIG. 3 illustrates subpixel interpolation based on only two pixel values. More general interpolation schemes based on many pixel samples for each subpixel interpolation can markedly reduce the interpolation more, although it will increase the hardware requirements, including the number of scans which must be stored. Standard interpolation schemes such as higher order polynomial fit or sin x/x interpolation can be implemented as a combination of PROMS (or RAMS) and adders.

Critical Dimension Corrector

Figure 5:
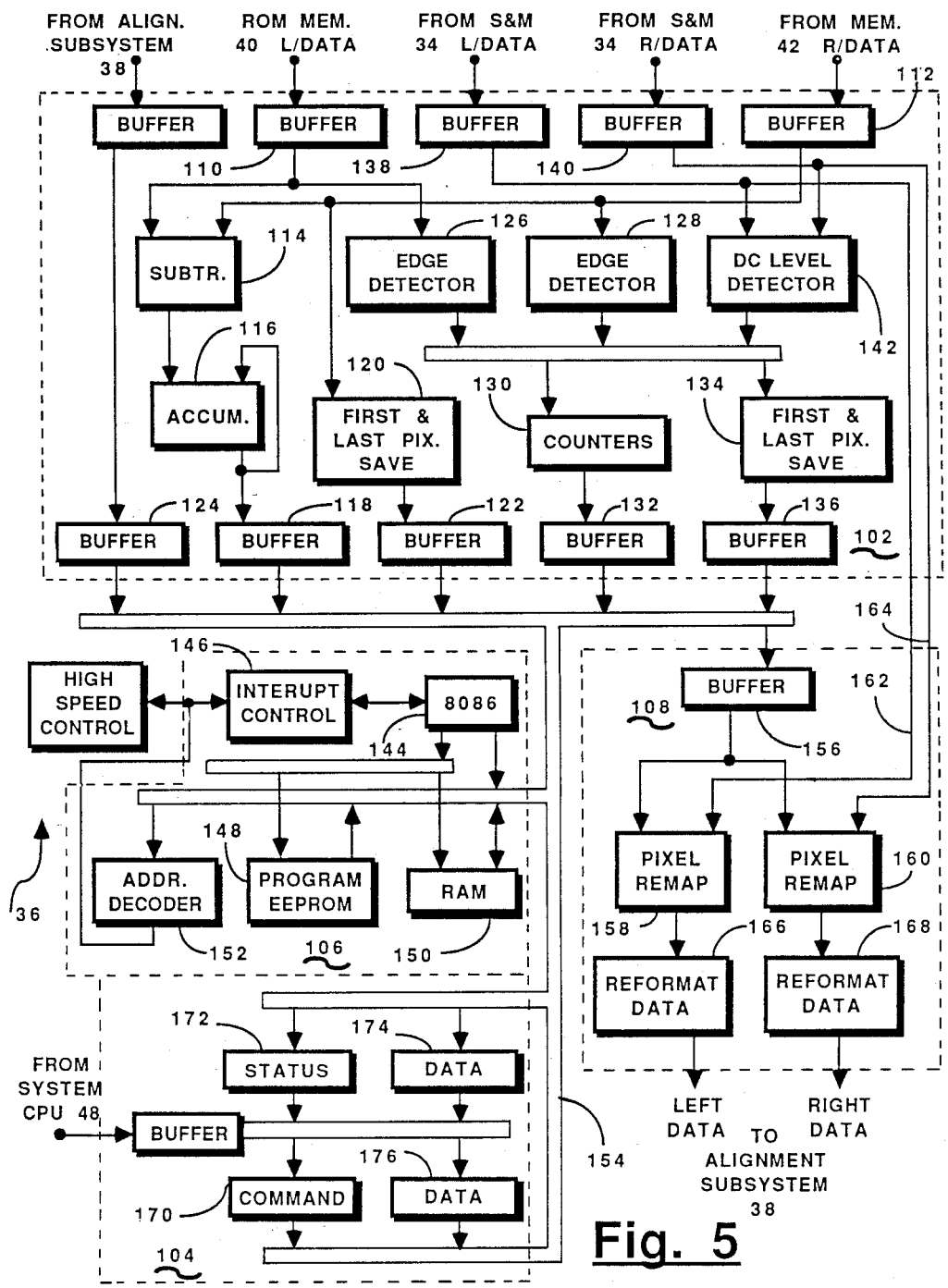
FIG. 5 is a block diagram illustrating the critical dimension (CD) corrector subsystem shown in FIG. 1.

In FIG. 5 of the drawing, the principle components of the critical dimension (CD/DC) corrector 36 are shown to include a data collector 102, a host interface 104, a measurement process 106, and CD/DC correction remapping hardware 108. As suggested above, the purpose of the corrector 36 is to make traces on the mask the same width in both data streams, i.e., it corrects for critical dimension variations which are process dependent. The nature of such critical dimension variations is outlined in FIG. 5a. Although slight variations in line width on the photo mask are permissible from the integrated circuit manufacturers viewpoint, such variations can make a substantial difference to the defect detection apparatus. Accordingly, steps must be taken to compensate for such variations before the data is input to the defect detector sub-system 44 so as to avoid the occurrence of false defects.

Generally speaking, the way in which corrector 36 functions is to integrate the total area of the trace lines over a broad window under one objective, and then do the same relative to the other objective. The basic assumption is then made that if the window is big enough, the area of any defects should be insignificant. The system thus adjusts the areas of the traces so that they are equal for both windows.

Figure 5B:
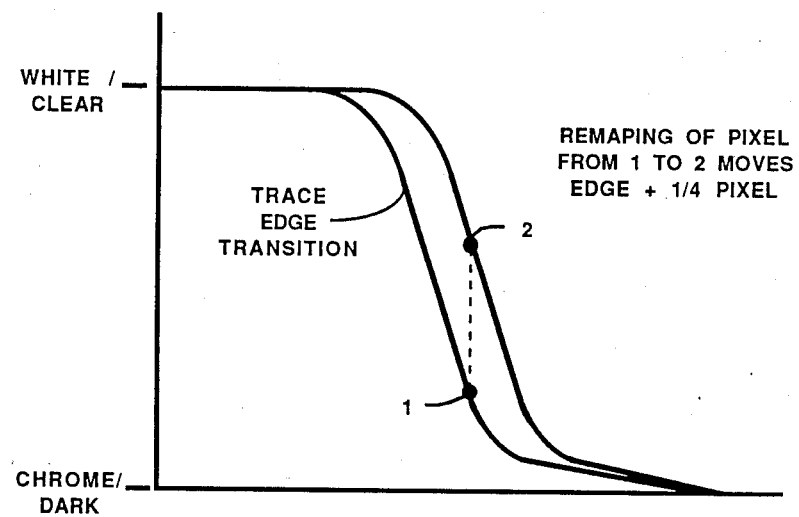
FIG. 5b is a diagram illustrating the S-curve remapping accomplished in accordance with the present invention.

The traces under the right objective and the traces under the left objective are both convolved with the Airy function. Thus, instead of having vertical sides that connect 15 level data with 0 level data, both sides have "S" curves, such as illustrated in FIG. 5b, that gradually transition from a clear area to an opaque or dark area. Because of process variations and possibly even optical variations from side to side, the width of the trace lines may not be the same. In order to make them the same, a determination is made that one side is too wide compared to the other side, and the system functions to shrink the wide side and simultaneously increase the width of the other side. This is believed to be preferable to increasing or decreasing the width of traces on a single side.

More specifically, during CD error measurement, the buffers 110 and 112 of data collector 102 respectively receive left data and right data from the mask memories 40 and 42. The difference between this data is taken by subtractor 114, and an accumulator 116 accumulates the difference for the entire scan. A buffer 118 then buffers it for use by the measurement processor 106.

At the same time, the first and last pixel is saved in memory 120 and made available via buffer 122 for pixel interpolation as recommended by the alignment subsystem 38 via buffer 124. Also during this time, edge detectors 126 and 128 determine if a pixel is on a vertical and/or horizontal edge for each of the left and right sides. These occurrences are counted by counter 130 and made available through a buffer 132 to the measurement processor 106 along with the first and last pixel edge information provided by memory 134 and buffer 136 for subpixel interpolation.

During DC correction, data collector 102 uses data input via buffers 138 and 140 from S & M corrector 34 to detect simultaneously, in a DC level detector 142, the 0s, 1s, Es, and Fs in either the left or right side. These occurrences are counted by counter 130 and made available to measurement processor 106 through buffer 132.

In the preferred embodiment, measurement processor 106 is comprised of a single chip 8086 microprocessor 144 with interrupt control 146, program EEPROM 148, RAM 150, and address decoding 152. The 8086, running its program in EEPROM, receives appropriate commands and information from the system CPU over bus 154, collects data from data collector 102 after each scan, and stores it in RAM 150. After a sufficient number of scans have been collected, this data is processed and a correction factor is output to the remap hardware 108 over bus 154.

The CD/DC correction remapping section 108 takes the correction factors input at buffer 156 from the measurement processor and applies them to the addresses of remapping proms 158 and 160, along with input data received on lines 162 and 164 from S & M corrector 34. The remapped output pixels are then reformatted at 166 and 168 and input to alignment subsystem 38 and scan delay circuits 37 and 39.

The system bus interface 104 allows the system CPU 48 (FIG. 1) to communicate with measurement processor 106 by use of a command register 170, a status register 172, and data registers 174 and 176. The system CPU initializes the CD corrector, provides run time parameters, and monitors subsystems status via this interface.

Alignment Subsystem

Figure 6:
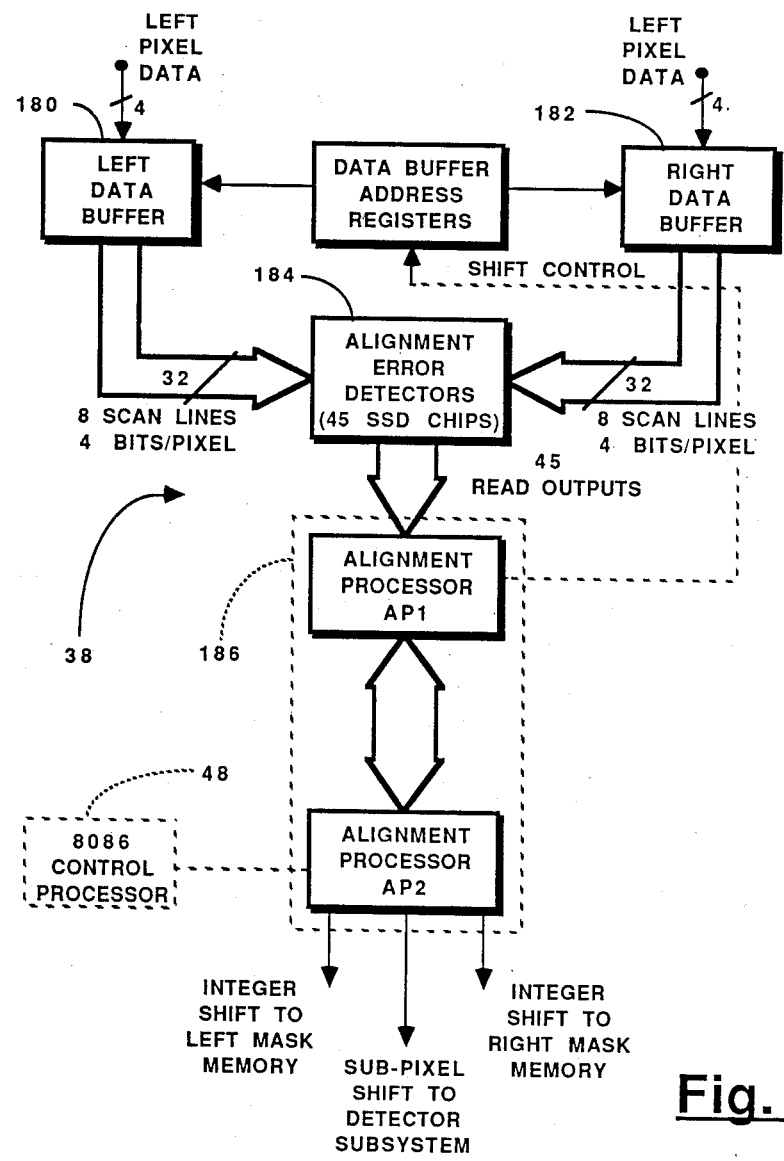
FIG. 6 is a simplified block diagram illustrating the principal components of the alignment subsystem shown in FIG. 1.

As indicated, the output of critical dimension corrector 36 is input to an alignment subsystem 38, the principal components of which are illustrated in FIG. 6 of the drawing. The data first enters the left and right data buffers 180 and 182, one vertical scan line at a time. The output of each data buffer is 8 vertical scan lines in parallel going into the alignment error detectors 184. An important feature of the data buffers is that they contain a sufficient number of scans so that one side can be shifted relative to the other up to 7 scans in either direction. This shift is under the control of the AP1 portion of alignment processor 186.

The alignment processor 186 finds the best alignment between the left and right images by shifting one image relative to the other in integral pixel amounts and then computing the sum of the squares of the difference image for each of the possible shifts. In this way, a sum of squared difference map (SSD) is computed for 225 combinations of X and Y integral shifts (from $-7$ to $+7$ pixels in both X and Y).

Alignment processor 186 is split into two parts (AP1 and AP2) simply because the processor as designed, even though using a fast bit-slice architecture, was not fast enough to perform the full interpolation task at full data rates. AP1 and AP2 are almost identical general-purpose bit-slice computers. The purpose of AP1 is to assemble the 15 by 15 SSD map, to average maps, to find the minimum of the averaged map, and finally to transfer that minimum and the 5×5 subarray centered on that minimum to AP2. AP2 communicates with the system controller as well as AP1, performs the subpixel interpolation, and outputs the integral shift and subpixel shift information to the other subsystems.

Figure 6A:
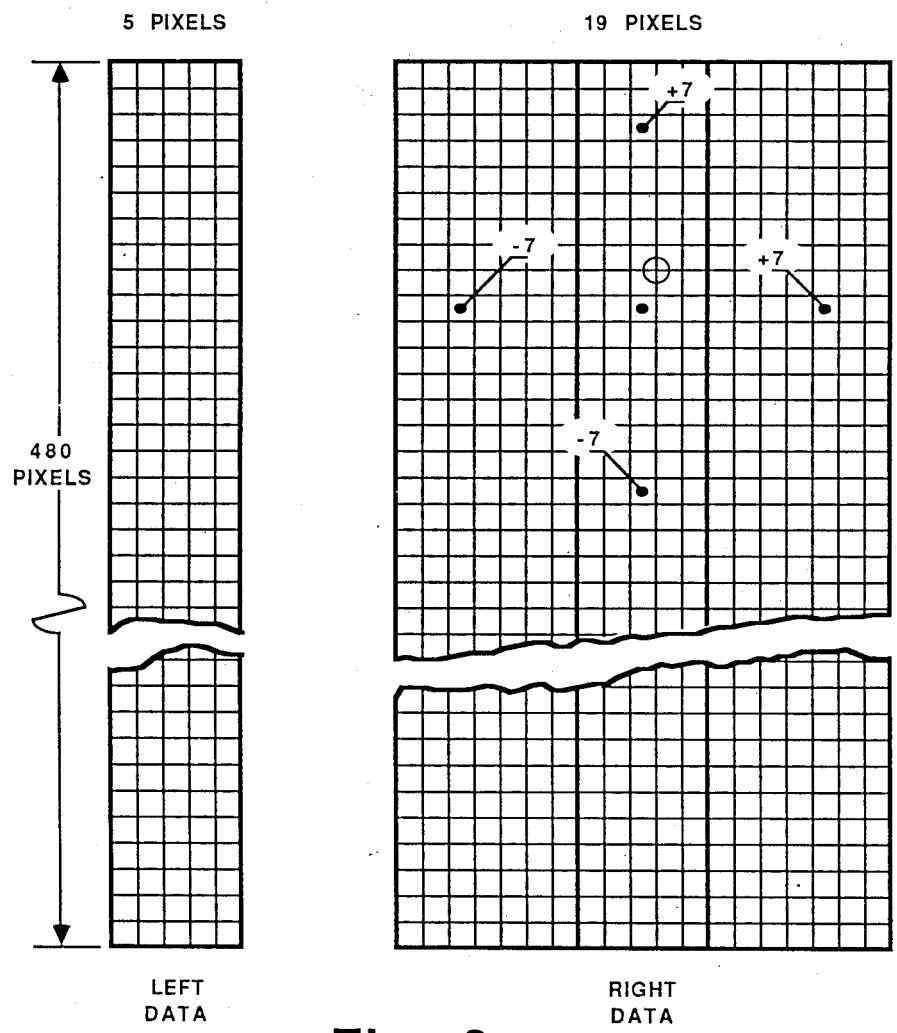
FIGS. 6a, 6b and 6c are diagrams illustrating the manner of operation of the alignment subsystem.

The alignment error detectors 184 contain 45 semi-custom gate array chips including the circuit discussed below with regard to FIG. 11. The circuits compute sum of squared differences at high speed, and each chip can compute the SSD of a strip 5 pixels wide by full sensor height in one scan time. Referring to FIG. 6a, the detectors 184 compare a strip of data 5 by 480 pixels on the left with a larger strip 19 by 480 pixels on the right. One SSD chip compares the whole left strip with the center 5 pixels of the right strip. Another SSD chip compares the same left strip with a 5 pixel wide section of the right strip displaced an integral number of pixels away from the first one. In principle, 225 SSD chips could be used to compute the 15 by 15 SSD map in one scan time. Since new data will not be available for 5 scan times, it is not necessary to compute all 225 values simultaneously. Consequently, only 45 SSD chips are used. After 5 scans and appropriate shifts of the data, all 225 values have been computed and read by AP1.

It will be noted that finding the minimum of the sum of squared differences is mathematically identical to finding the maximum of the cross correlation function except for differences in handling edge effects.

Based on the 5×5 submatrix of the SSD map containing the minimum value, AP2 first determines which of three cases apply:

Case A: There is geometry present in the correlation window with more than one angle of line represented. In this case, it is assumed that the SSD surface is locally parabolic. The displacement is found by fitting a parabola to the data represented by the minimum point and its 8 surrounding points, and computing the location of the minimum of this parabola using first and second partial derivatives.

Case B: There is geometry present in the correlation window with only one angle of line represented. In this case, it is assumed that the SSD surface has a locus of minima which form a straight line. Rather than jumping to the absolute minimum point (which may be determined by random noise), the algorithm chosen is to move from the previously determined point in a direction perpendicular to the line (minimum Euclidean distance).

Case C: No geometry in the correlation window. In this case, no change is made until new geometry appears in the window on both sides.

The advantages of using an alignment system employing full two-dimensional cross correlation are:

It will align to any type of geometry. e.g. circles, dogbones, arbitrary curves with or without straight line segments.

It works well without full modulation from black to white.

This is important for narrow linewidths and masks with poor contrast ratios (such as iron oxide).

Although the preferred embodiment of the alignment error detectors uses a sum of squared differences approach, it will be appreciated that other functions of the differency could also be used.

AP2 Overview

AP2 receives from AP1 the necessary data in the sum of squares difference (SSD) map to make a decision as to what values of skew (or offset) should be sent to the mask memories 40 and 42, and the defect detector 44. The SSD map provides the sum of squared differences of the left and right side images at different integral pixel offsets. The sum is over a ten scan wide by active sensor tall window. In the preferred embodiment detections on each side is accomplished by a sensor array that is 1 pixel wide by 480 pixels tall. At each corresponding pair of pixels the difference is calculated, squared and added into the accumulator. The sums of squares are calculated in the 'macro cells' in the alignment error detectors 184, and are read by AP1.

There are three fundamental operations AP2 performs before it sends skew values to the mask memories and defect detectors. AP2 uses an interpolation algorithm upon the SSD values at the different integral shifts to find the 'best' offset to a fraction of a pixel. 'Best' offset means the shift of one image relative to the other which would achieve the minimum sum of squares over the window being considered. Secondly, AP2 evaluates the reliability of the sample, generating a weighting factor to quantify its confidence in that sample. Finally, AP2 low-passes the sequence of skew values, since it is only responsible for correcting mechanical misalignment, which varies slowly as a function of time.

The defect detector 44 as currently designed can handle only positive fractional offsets, while the mask memories 40 and 42 can be shifted in integral steps only. Therefore, the calculated skew is formatted into a positive fraction and an integral value. The former is sent to the defect detector and the latter is sent to the mask memories.

Another function of AP2 is to provide an interface to the outside world for the alignment subsystem 38 via a bus interface to the system CPU 48.

AP2 Interpolation

During the scanning of a plate, AP2 receives from AP1 a 5×5 portion of the SSD map centered around the minimum value in the 15×15 array which AP1 reads from the alignment error detectors 184. Along with this information come the coordinates for the center of the 5>5 subarray.

Based upon the knowledge of the SSD map at the integral offset points, AP2 models the surface of a continuous SSD function as a second order function of the skew variables (x and y). The position where this function attains a minimum provides the skews which align the two images by the least squares criterion.

Subpixel Interpolation General Theory

Subpixel interpolation is achieved by modeling the SSD map close to its minimum by a parabolic surface that is a second order equation in x and y. This equation is the two dimensional Taylor Series about the minimum point which is at (SSD(2,2). The SSD map and the estimates for the derivatives are as follows:

The SSD map is a 5×5 which is shown below centered at (x,y)=(2,2). (In the code, the map is given as SSDYX., for row and column).

| SSD(0,0) | SSD(0,1) | SSD(0,2) | SSD(0,3) | SSD(0,4) |
|---|---|---|---|---|
| SSD(1,0) | SSD(1,1) | SSD(1,2) | SSD(1,3) | SSD(1,4) |
| SSD(2,0) | SSD(2,1) | SSD(2,2) | SSD(2,3) | SSD(2,4) |
| SSD(3,0) | SSD(3,1) | SSD(3,2) | SSD(3,3) | SSD(3,4) |
| SSD(4,0) | SSD(4,1) | SSD(4,2) | SSD(4,3) | SSD(4,4) |

Given the above map, the estimates for the derivative are:

$$\partial z/\partial x = (SSD(2,3) - SSD(2,1))/2$$
$$\partial z/\partial y = (SSD(3,2) - SSD(1,2))/2$$
$$\partial^2 z/\partial x^2 = SSD(2,3) + SSD(2,1) - 2 \cdot SSD(2,2)$$
$$\partial^2 z/\partial y^2 = SSD(3,2) + SSD(1,2) - 2 \cdot SSD(2,2)$$
$$\partial^2 z/\partial x \partial y = SSD(3,3) + SSD(1,1) - SSD(1,3) - SSD(3,1)$$

The SSD function can be expressed as:

$$f = Z_0 + x(\partial z/\partial x) + y(\partial z/\partial y) + (\tfrac{1}{2})x^2(\partial^2 z/\partial x^2) + (\tfrac{1}{2})y^2(\partial^2 z/\partial y^2) + xy(\partial^2 z/\partial x \partial y)$$

where $Z = SSD(y,x)$, $z_0 = SSD(2,2)$, and all partials are taken at $(y,x)=(2,2)$.

At the minimum the gradient must be zero. Therefore:

$$\partial f/\partial x = \partial f/\partial y = 0,$$

which implies:

$$\partial z/\partial x + x(\partial^2 z/\partial x^2) + y(\partial^2 z/\partial x \partial y) = 0$$

$$\partial z/\partial y + x(\partial^2 z/\partial x \partial y) + y(\partial^2 z/\partial y^2) = 0$$

Thus:

$$x(\partial^2 z/\partial x^2) + y(\partial^2 z/\partial x \partial y) = -(\partial z/\partial x)$$

$$x(\partial^2 z/\partial x \partial y) + y(\partial^2 z/\partial y^2) = -(\partial z/\partial y)$$

Flatmap Case

If all of the coefficients are zero, then any value of x and y will solve the equations, which implies that all points have the same SSD. In this case, which will be referred to as the flatmap case, there is no information and so AP2 will maintain the current skew values.

One Dimensional Cases

If the coefficients of one of the two equations are a linear multiple of the coefficients of the other equation, then there is a line along which every point has the minimum value achieved by the SSD function. That is, if for some constant $\mu$:

$$(\partial^2 z/\partial x^2) = \mu(\partial^2 z/\partial x \partial y)$$

and $$\mu(\partial^2 z/\partial y^2) = (\partial^2 z/\partial x \partial y)$$

or equivalently:

$$(\partial^2 z/\partial x^2)(\partial^2 z/\partial y^2) - (\partial^2 z/\partial x \partial y)^2 = 0$$

If the above condition is true, we say that the pair of linear equations are dependent. If the equations are indeed dependent, and at least one of the coefficients is non-zero (i.e., not the flatmap case), then we have information in only one direction. It is desirable to correct the skew only in the direction where there is information, while making no change in the direction orthogonal to that in which there is no information. Note that the direction in which there is information need not be parallel to one of the axes.

Two Dimensional Case

The final case is where there is two dimensional information which is determined by the pair of linear equations being independent. In this case there is a unique minimum point for best least squares alignment.

SUBPIXEL INTERPOLATION IN THE ALIGNMENT PROCESSOR

Flatmap Case (No Information)

The interpolation code begins by calculating the pure second derivative in both x and y. By testing these values against thresholds provided by the system software, AP2 decides whether or not the value is significantly greater than zero. If both are insignificant, then the flatmap case is applied, leaving the skew values unchanged.

One Dimensional Manhattan Geometry

Because of the manner in which AP1 finds the center of the 5×5, we know that the function being modeled is in the vicinity of a local minimum or flat. This implies that if the second derivative in one of the variables is zero, then the first derivative in that variable is also zero; otherwise, we would not be at a minimum since the function would decrease in one of the directions parallel to the axes whose second derivative is zero. The mixed partial $(\partial^2 z/\partial x \partial y)$ must also be zero, or we would have a saddle point.

If the only one of the pure second derivatives is significant, then AP2 does a purely one dimensional interpolation as follows (assume that it is in x):

$$\partial f/\partial x = 0 = \partial z/\partial x + x(\partial^2 z/\partial x^2)$$

and so:

$$x_{min} = -(\partial z/\partial x)/\partial^2 z/\partial x^2$$

The Ridge Case

If both second derivatives are significant, it is still necessary to determine whether there is two dimensional information by checking the linear dependence of the two linear equations. For this it becomes necessary to calculate the mixed second order partial derivative. If the dependence condition (the single equation condition) is close to singular, as determined by a threshold provided by the system software, then one enters the ridge case.

Figure 6B:
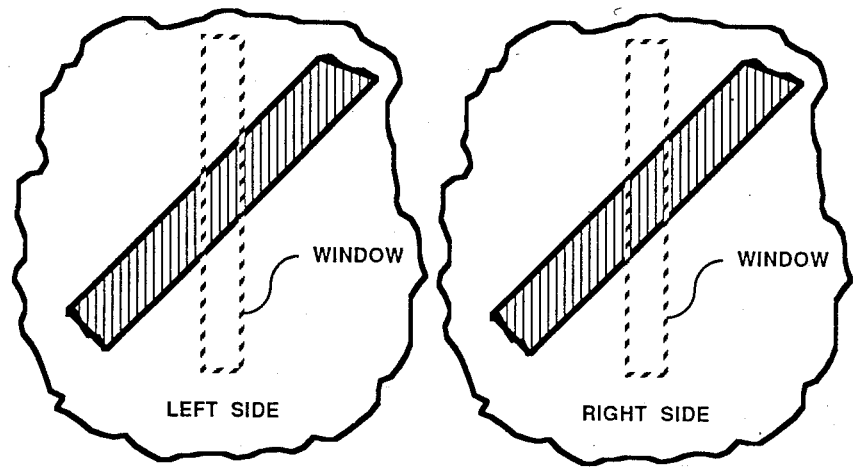

In the ridge case, AP2 is dealing with a one dimensional problem in a non-Manhattan direction. As illustrated in FIG. 6b, that there are many x-y shifts where these two images would appear perfectly aligned when only looking within the windows.

The ridge case assumes that there exists a line at which the SSD function attains the same minimum, which will be referred to as the ridge line. However, AP1 does not know this and could pick out a minimum along the ridge line which is 'far' from the current alignment point. Though the skew calculated from this somewhat arbitrarily chosen local minimum along the ridge line might be on the actual ridge line, it will violate the desire to move only perpendicularly to the ridgeline; that is, move only in the direction in which there is information. In fact, the skews could go crazy since the movement along the ridge would be out of control.

Figure 6C:
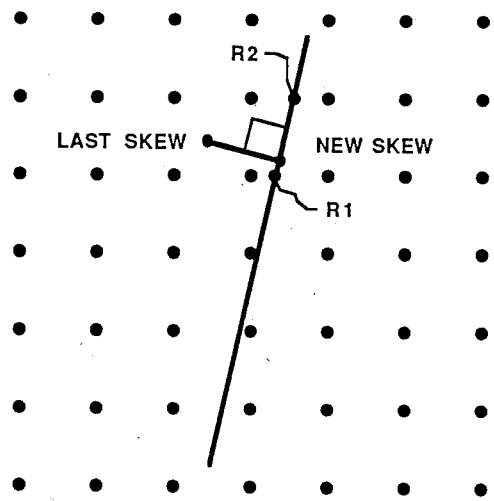

Therefore, the ridge case is handled by doing two one dimensional interpolations for minimums at two different points along the ridge line. The new skews are determined by the point along the ridge line which is closest to the old skew values; that is, the orthogonal projection of the old skew point onto the ridge line. (If the two points are sufficiently far apart, one will get a good fit for the ridge line and there should not be any creeping parallel to the ridge). As a further guarantee against creeping, one always uses the same point as the starting position for calculating the new skew, as long as one remains in a sequence of ridge cases. This point is the last known skew before entering the sequence of ridge cases, and is called last skew. (see FIG. 6c).

In order to accomplish this, it is first necessary to decide which direction (x or y) has the most information, so that direction can be used for the interpolation. This is determined by finding the maximum of the second derivatives. For example, if the x second derivative is larger, then one point along the ridge line will be determined by a one dimensional interpolation in the x direction around the minimum, giving the point $R_1 = (y_2, x_2)$ (See FIG. 6c).

The equation of the line passing through $R_1$ and $R_2$ is:

$$(\Delta y / \Delta x) = (y - y_1)/(x - x_1)$$

where $\Delta x = x_2 - x_1$, and $\Delta y = y_2 - y_1$

A line perpendicular to this will have a slope of $-(\Delta x / \Delta y)$. Therefore, the equation of such a line passing through the point lost skew $= (x_{ls}, y_{ls})$ is:

$$-(\Delta x / \Delta y) = (y - y_{ls})/(x - x_{ls})$$

The above two equation then become:

$$\Delta yx - \Delta xy = \Delta yx_1 - \Delta xy_1$$

$$\Delta xx - \Delta yy = \Delta yy_{ls} + \Delta xx_{ls}$$

Since $|\Delta y| = 1$ and $(\Delta x)^2 \geq 0$, there is a unique solution to the pair of linear equations. (See the conditions above which determined whether the original linear equations had a unique solution. Here the condition is $(\Delta \mu)^2 + (\Delta x)^2 \; 0$ Thus, the coordinates of the new skew are given by:

$$x_{nx} = (\Delta x \Delta y (y_{ls} - y_1) + (\Delta y)^2 x_1 + (\Delta x)^2 x_{ls})/((\Delta x)^2 + (\Delta y)^2)$$

$$y_{ns} = (\Delta x \Delta y (x_{ls} - x_1) + (\Delta y)^2 y_{ls} + (\Delta x)^2 y_1)/((\Delta x)^2 + (\Delta y)^2)$$

If the equation used to determine whether the ridge case applies is non-zero, then there is a unique solution to the pair of linear equations which came from setting the gradient equal to zero. The solution is:

$$x_{min} = ((\partial z/\partial y)(\partial^2 z/\partial x \partial y) - (\partial z/\partial x)(\partial^2 z/\partial y^2))/\text{denom}$$

$$y_{min} = ((\partial z/\partial x)(\partial^2 z/\partial x \partial y) - (\partial z/\partial y)(\partial^2 z/\partial x^2))/\text{denom}$$

Where:

$$\text{denom} = (\partial^2 z/\partial x^2)(\partial^2 z/\partial y^2) - (\partial^2 z/\partial x \partial y)^2$$

Weighting Factor

Since a large defect could cause severe misalignment, the processor determine how closely the two sides match, generating a weighting factor, referred to as "goodness". The value of the SSD function at the minimum, normalized by the number of edges, provides an indication of how well the two sides match. The normalization factor is the sum of the pure second derivatives, which provides a measure, up to a constant multiple, of the number of edges in the SSD window. The normalized minimum value is then used via a look-up table, filled by the system software, to provide the weighting factor. This factor tells how much weight to give the new sample in the weighted average of the old and new skew.

Single Pole Filter

Since AP2 is responsible for correcting only low frequency, mechanically induced changes in skew, the skew values are low passed using a single pole filter. The filter's time constant is provided by the system software.

For each iteration of the skew calculations the new skew value is calculated as a weighted average of the old skew value and the new skew value (separately for x and y), as follows:

| | |
|---|---|
| newskew = | 1/(time constant) * goodness * newdkew + (1 − 1/(time constant)) * goodcnt * oldskew |
| goodcnt = | 1/(time constant) * goodness + (1 − 1/(time constant)) * goodcnt |
| newskew = | newskew/goodnt |

Finally, the new skew is formatted to provide the mask memories 40 and 42 with an integral skew, while passing on the positive fractional skew in the range from zero to one to the defect detector 44.

Database Mode

In the database mode, AP2 keeps track of the minimum and maximum y skew. At the end of the swath, the system software reads the values for minimum and maximum y skew, using them to adjust the sensor position with respect to the database image.

In the database mode, AP2 controls the plus or minus frequency modulation (FM) lines, (not shown), of the system. The FM is used to correct x runout in database mode. When asserted, FM causes the RIA clocks (not shown) to be stretched or shortened such that a skew change of 1/74th of a pixel is made on each scanline. FM is enabled whenever the absolute value of the x skew exceeds two.

Defect Detector

Figure 7:
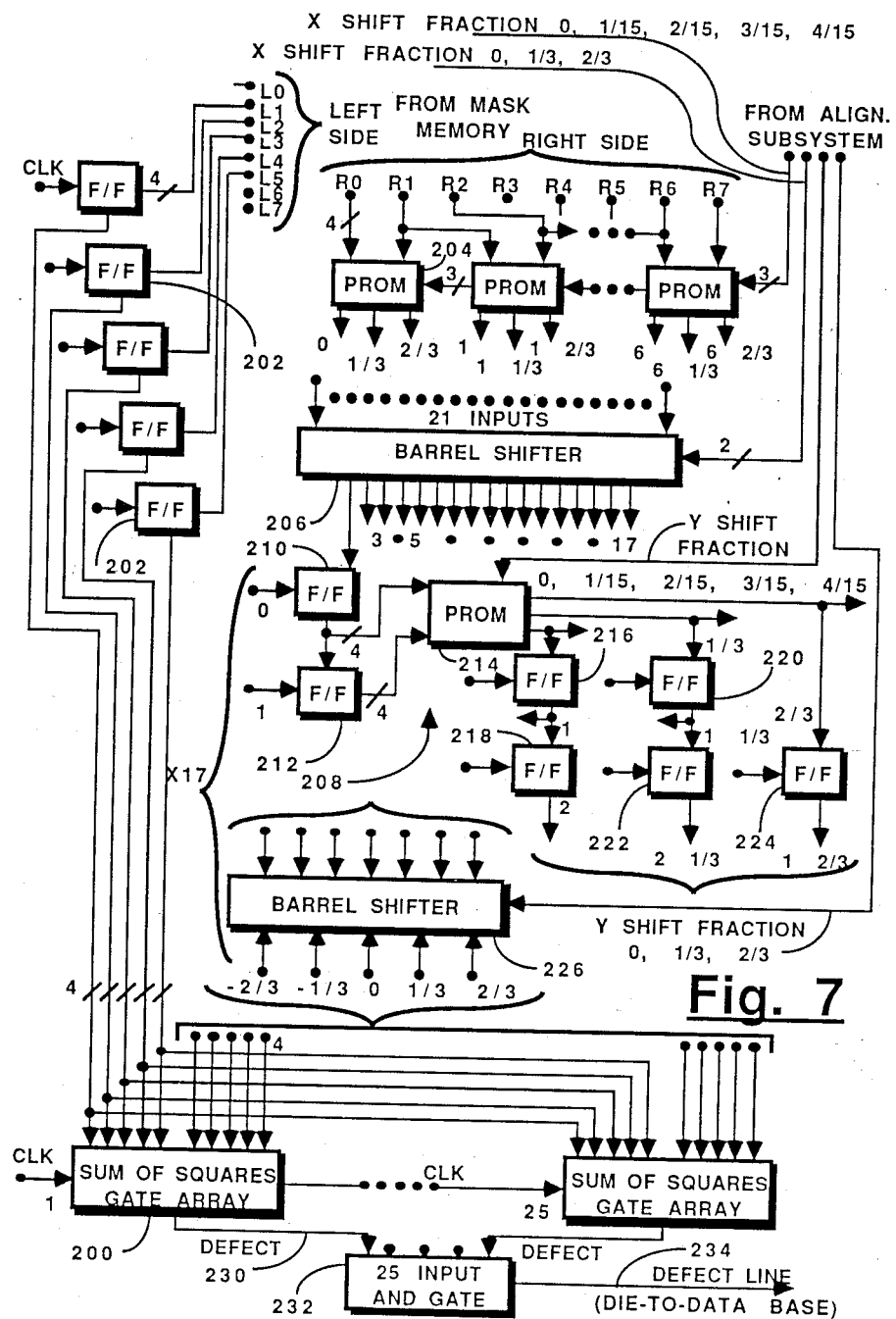
FIG. 7 is simplified block diagram illustrating a portion of the defect detector subsystem of FIG. 1.
Figure 8:
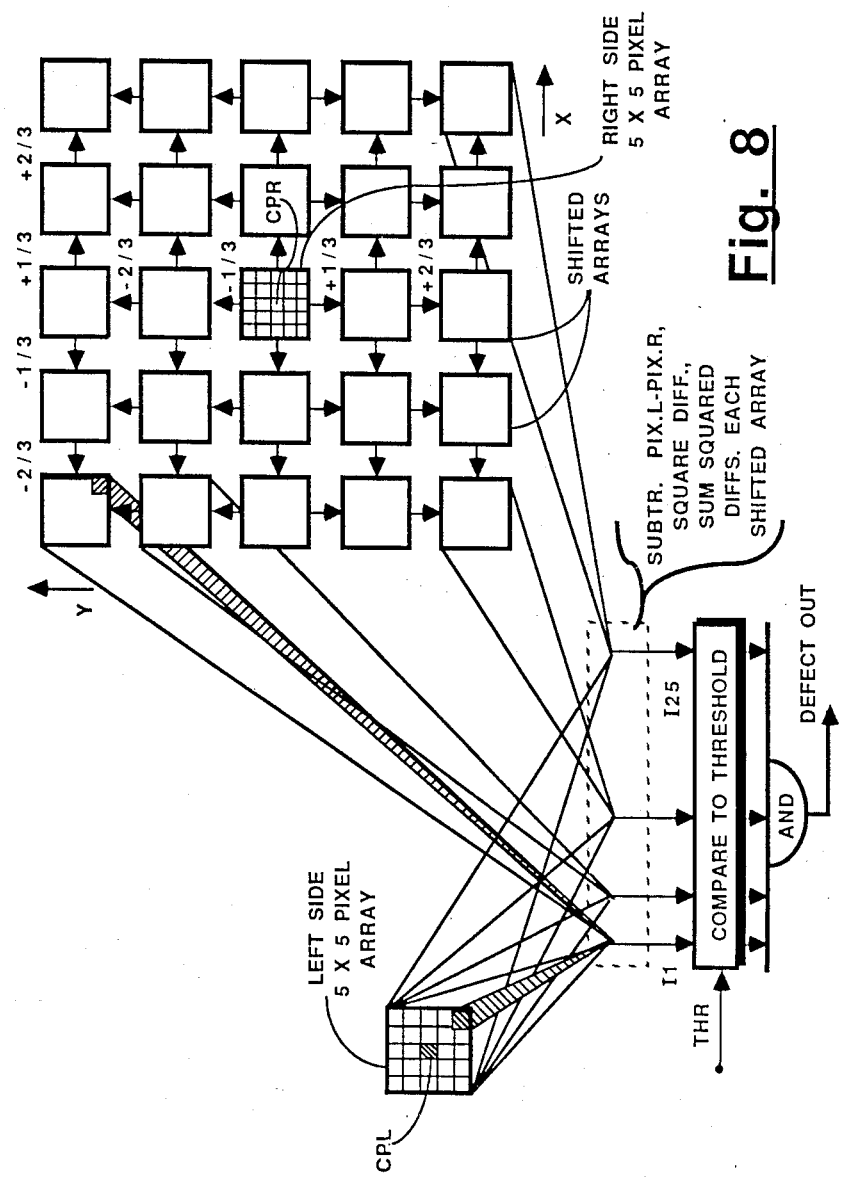
FIG. 8 is a diagram illustrating operation of the detector portion shown in FIG. 7.
Figure 9:
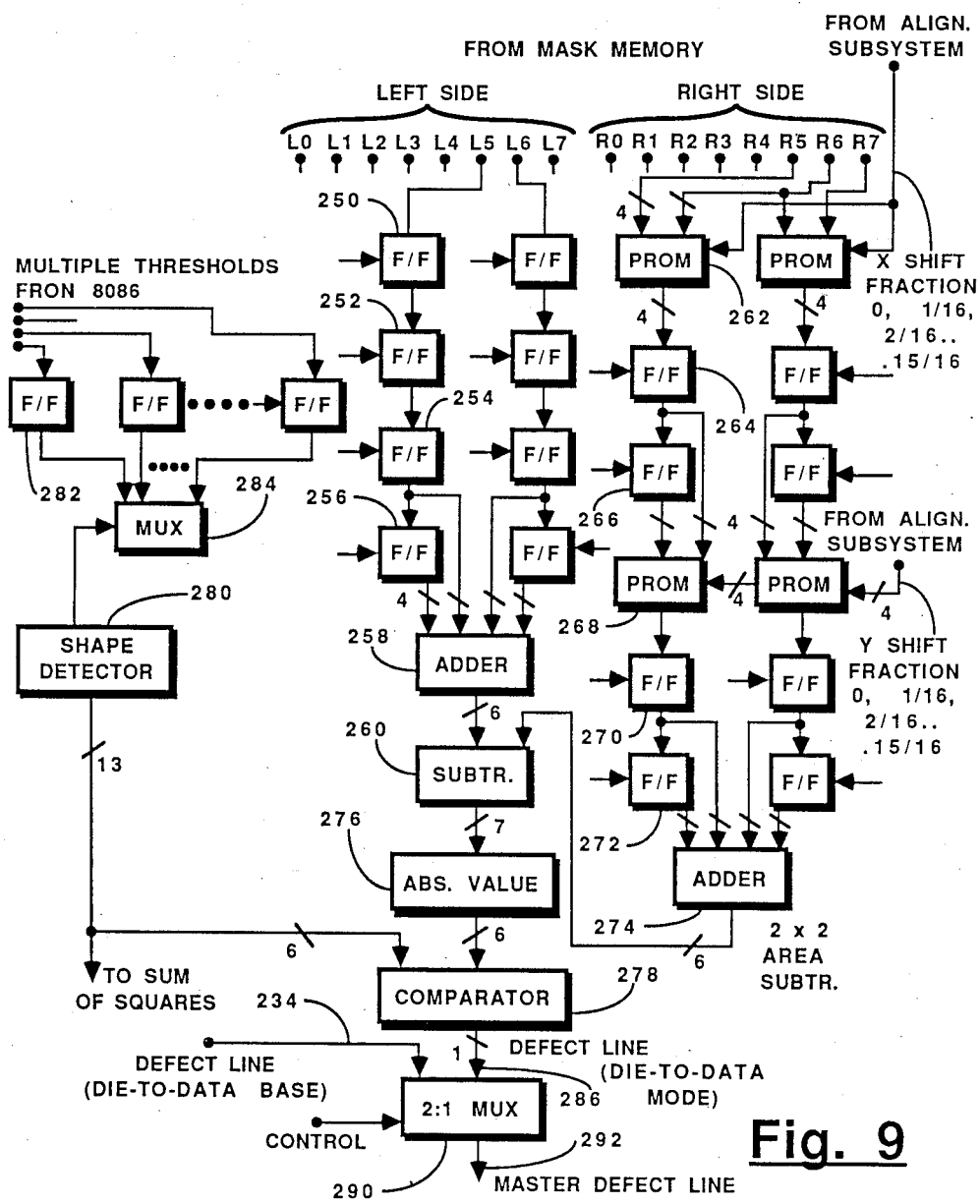
FIG. 9 is a simplified block diagram illustrating a second portion of the defect detector subsystem of FIG. 1.

As suggested above, the defect detector subsystem 44 (FIG. 1) is actually comprised of two detector sub-circuits which are separately shown in FIGS. 7 and 9 of the drawing. In FIG. 7, an nxn logic circuit implementing a sum-of-squared differences detector (SSD) is shown for the example where n=5. This detector is normally used for die-to-data base detection, but can also be used for die-to-die evaluations. In order to better understand the concept implemented by the circuit illustrated in FIG. 7, reference is made to FIG. 8 which is a diagram graphically representing a 5×5 pixel array centered on the pixel CPL from the left data stream, and a corresponding right side 5×5 pixel array centered on the pixel CPR.

As illustrated by the arrows, each pixel of the right side array is variously shifted in increments of $\frac{1}{3}$ of a pixel in both directions in both X and Y so as to form 24 additional arrays the data of which is offset by the indicated sub-pixel shifts. Each pixel of the left side array is then subtracted from each pixel from each shifted right side array, the difference is squared, and the squared differences are summed. The summed values are then compared to a threshold THR to generate a defect or non-defect signal at one of the 25 inputs I1–I25 to the illustrated AND gate.

If all of the inputs to the AND gate indicate a defect, then the AND gate will generate a defect output signal. However, if any single input to the AND gate indicates no defect, then the AND gate will output a signal indicating no defect. For purposes of clarification it will be understood that the illustrated left side array of FIG. 8 might correspond with the array of pixels shown in FIG. 2 centered on the pixel L36.

Returning now to FIG. 7, it will be noted that the circuit implementing the 5×5 detector sub-circuit includes 25 sum-of-squares gate arrays 200 (discussed below with reference to FIG. 11), each of which receives five four-bit pixel inputs from the left side data stream and five four-bit pixel inputs from the right side data stream received from the mask memories 40 and 42 respectively, depicted in FIG. 1. Each of the gate arrays 200 performs the sum-of-squares detection function discussed above relative to FIG. 8. Data from the left side data stream is received by registers 202 which simultaneously clock data from the pixels in columns L1–L5 into each of the gate arrays 200. It will thus be appreciated that during any five clock interval a 5×5 left side array, such as that illustrated in FIG. 2, will be resident in each of the gate arrays 200.

In order to perform the right side array shifts illustrated in FIG. 8, data from each of the 8 scanned columns (similar to those illustrated in FIG. 2 for the left side) are input in contiguous pairs to seven PROMs 204 which are caused by an input from alignment subsystem 38 (FIG. 1) to output three sets of shifted data for input to 3 of the 21 inputs of a barrel shifter 206. Under control of alignment subsystem 38 barrel shifter 206 outputs shifted data to each of 17 circuits one of which is illustrated at 208 and includes a pair of flip-flops 210 and 212, a PROM 214, 5 additional flip-flops 216–224, and a barrel shifter 226. PROM 214 performs the same type of function performed by PROM 204 except that it provides 3 subpixel shifts in the vertical scanning direction instead of the horizontal direction. Integral shifts in the vertical direction are accomplished by clock delays through the flip-flops 216–222.

Each of the sub-circuits 208 will output 5 sets of 4-bit data which is fed into a corresponding one of the gate arrays 200 causing each of the gate arrays to have resident therein, in addition to the 5×5 left side array, data corresponding to one of the 5×5 shifted arrays illustrated in FIG. 8, and one will have the unshifted array centered on the pixel CPR, also illustrated in FIG. 8. The gate arrays then perform their sum-of-squared differences evaluation and develop outputs on the 25 input lines 230 to AND gate 232 which in turn develops defect or non-defect signals on its output defect line 234 as explained above relative to FIG. 8.

It is to be understood that, although the diagrams and descriptions above refer to a 5×5 shift pattern of 5×5 SSD arrays shifted in increments of $\frac{1}{3}$ and $\frac{2}{3}$ pixel in both dimensions, other shift patterns with different sub-pixel shift increments and different sized SSD arrays could also be used. Furthermore, instead of sum of squared differences, other functions of the differences could also be used in the defect detector subsystem.

Figure 10:
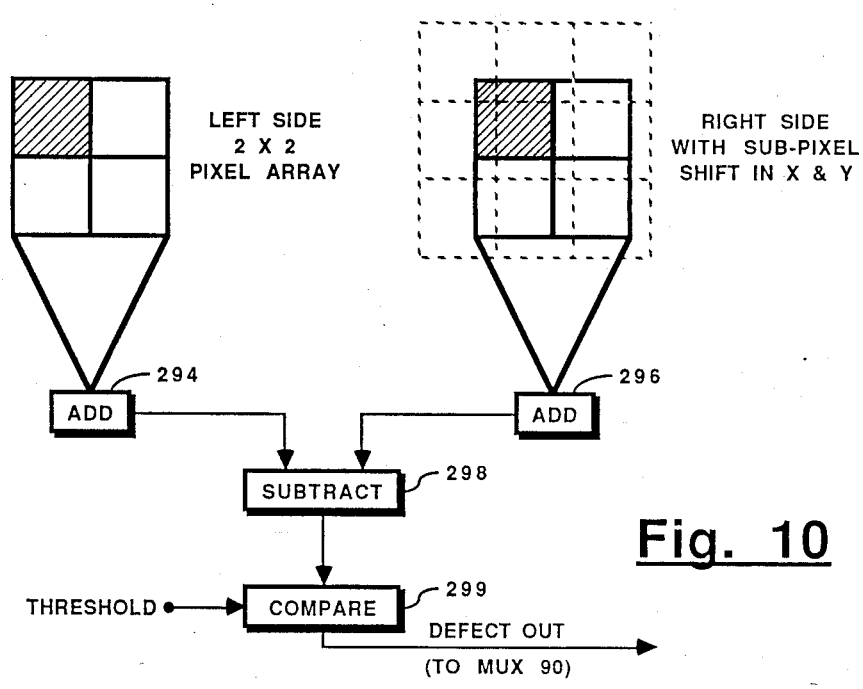
FIG. 10 is a simplified diagram illustrating operation of the detector portion illustrated in FIG. 9.

In FIG. 9, the second portion of detector subsystem 44 is depicted in block diagram form and has as its purpose to implement a 2×2 area subtraction detection of the scanned data. Departing momentarily, as illustrated conceptionally in FIG. 10, a 2×2 pixel array from the right side data stream is shifted vertically (y) and/or horizontally (x) in 1/16 pixel increments under control of the alignment subsystem 38 to a shifted position determined by the subsystem calculations. In performing the analysis, the pixel content of the depicted left array are each added as indicated at 294 and 296, the sums are subtracted at 298, and the absolute value of the difference is compared to a threshold at 299. If the absolute value of the difference exceeds the input threshold value, then a defect signal will be output.

Returning now to FIG. 9, a simplified block diagram of an implementation of the 2×2 subtraction detector portion of subsystem 44 will be described. As illustrated, data from pixel columns L5 and L6 is input to a series of registers 250–256 and shifted therethrough to an adder circuit 258. Note that in addition to the output of flip-flops 256, the outputs of flip-flops 254 are also input to the adder circuit 258. As a consequence, data corresponding to a 2×2 pixel array from the left side data stream is simultaneously input to the adder 258, and the sum of the content of each of the 4 pixels is output for application to one of the inputs of the subtracter circuit 260.

In the upper right hand corner of the figure it will be noted that in the right side stream, data from pixel columns R5, R6 and R7 is input in adjacent pairs to two PROMs 262 which cause the data to be shifted horizontally in increments of 1/16 of a pixel. The shifted data streams are then passed through registers 264 and 266, and into pair of PROMs 268. Note that the outputs of registers 264 are also input to the PROMs 268. Under control of the alignment subsystem 38 (FIG. 1), the PROMs 268 cause the data streams to be vertically shifted (in increments of 1/16 of a pixel) and the shifted pixel data is output through registers 270 and 272 to an adder circuit 274. Note that the outputs of the registers 270 are also input to the adder 274. As a consequence, the output generated by adder 274 will be serial data corresponding to the sum of the right side 2×2 pixel array (which is shifted 0 to 15/16th of a pixel in the horizontal and vertical directions). The output of adder 274 is then subtracted from the output of adder circuit 258 by the subtraction circuit 260, and the absolute values of the differences are output by circuitry 276 and input to one side of a comparator 278.

If the output of the absolute value circuit 276 exceeds the threshold applied to comparator 278, a defect signal will be generated on defect line 286.

Although FIG. 9 illustrates subpixel shifting by means of bilinear interpolation, higher degree polynomial fitting or sin x/x interpolation could be substituted for an increase in accuracy.

This circuit also includes a shape detector 280, which causes 1 of several threshold values received from the control processor 48 (FIG. 1) to be input through the registers 282 and a mux 284 to comparator 278. The shape detector 280 detects the number of edge pixels within and adjacent to the detector window and/or determines whether the geometry in the window is a single edge of a trace, both edges of a trace, a corner, a clear field, or an opaque field. Different thresholds are predetermined for each of these situations. The shape detector 280 determines, by logic contained in PROMS and PALS, which of these situations prevails at a given pixel time and selects the appropriate threshold value to be sent to the comparator 278 or to each of the sum of squared differences gate arrays 200 in FIG. 7.

Note that the threshold applied to comparator 278, or to the threshold inputs of each of the sum of squared differences gate array chips 200 of FIG. 7, is dynamic. It can change for every pixel time.

In order to allow the detector subsystem 44 to output either the output of the sum-of-squares comparison signal from line 234, or the area subtraction output from line 286, a 2:1 mux 290 is provided which will output the selected signal on the master defect line 292.

Figure 11:
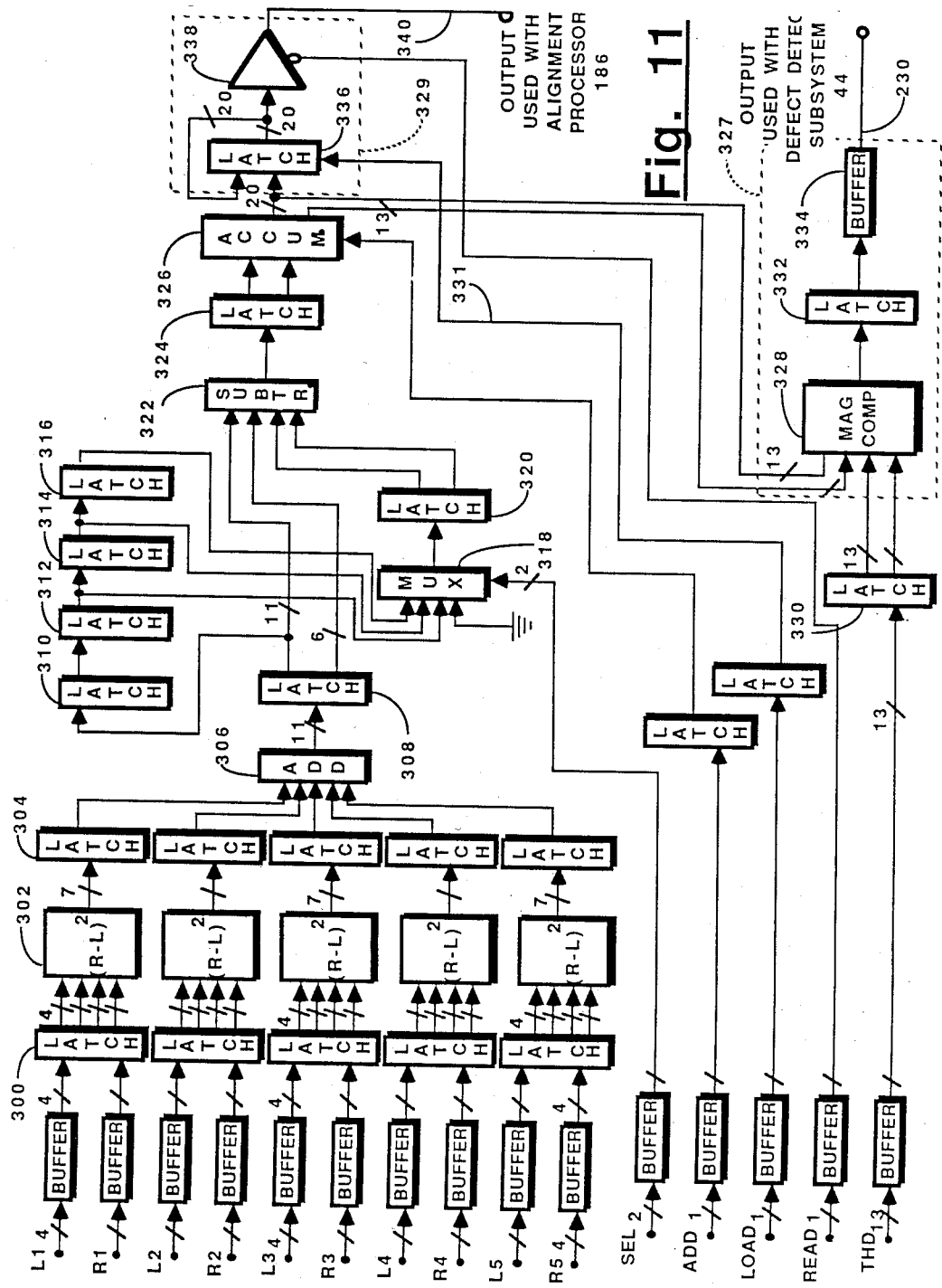
FIG. 11 is a simplified block diagram illustrating the principal components of a sum of squares gate array in accordance with the present invention.

In FIG. 11 a block diagram of one of the sum of squares gate arrays shown at 200 in FIG. 7 is illustrated. As will be discussed below, the gate array is also used in the alignment subsystem 38 (see FIG. 6). As shown, five sets of pixel data from the left side (L1–L5) and five sets of shifted data from the right side (R1–R5) are buffered and input to latches 300 and temporarily held for subsequent input to the subtracting and squaring circuits 302. The absolute values of the squared differences are then fed into latches 304 and subsequently into an adder 306 which outputs the sum of squared differences for five adjacent pixels. The sum is then input to a latch 308 which is available for input to a subtractor 322, and is simultaneously input to a series of latches 310 through 316. The data stored in latches 312, 314 or 316 can be selected in response to an input signal SEL and stored in a latch 320 for subsequent input to the subtractor 322.

By means of the elements 310 through 322, in response to a particular input signal SEL, the device can be operated in any of at least four modes, i.e., n×5 sum of squares, n×4 sum of squares, n×3 sum of squares, and n×m sum of squares with continuous accumulation; where n equals 1 to five and m can be any number, limited only by the size of the accumulator 326. Depending upon the mode selected, data is passed through latch 324 and accumulated in accumulator 326.

After accumulation, the data is input to either or both of two subcircuits 327 and 329. In 327 the accumulated data signal is input to a magnitude comparator 328 for comparison to a threshold input at THD, buffered and passed through a latch 330 into the comparator 328. The defect/no defect signal is then latched in 332 and buffered in 334 before being output to line 230 (FIG. 7).

In response to a LOAD at 331 the accumulated data can also enter the circuit 329 through a latch 336 and be output at 340 through a tri-state buffer 338. This is the output used in the 45 SSD circuits included in the alignment error detectors 184.

Although the present invention has been described above with respect to presently preferred embodiments illustrated in simple schematic form, it is to be understood that various alterations and modifications thereof will become apparent to those skilled in the art. It is therefor intended that the appended claims be interpreted as covering all such alterations and modifications as fall within the true spirit and scope of the invention.

What is claimed is:

1. A method of detecting defects in objects such as photomasks, reticles, wafers, printed circuit boards, and the like, comprising the steps of:
    inspecting a selected surface area of an object and generating a first stream of data having signal values representing the image content of each pixel thereof;
    generating a second stream of data having signal values representing the image content of each pixel of said second stream of data;
    storing corresponding portions of the first and second streams of data in memory;
    detecting with a resolution to a fraction of a pixel any misalignment between the stored portions of said first and second streams of data;
    aligning the stored first and second portions of data using subpixel interpolation to correct any detected misalignment therebetween; and
    comparing corresponding subportions of the stored and aligned first and second portions of data to detect differences therebetween, and upon detecting a difference, indicating the presence of a defect at a particular pixel location on the inspected object.

2. A method as recited in claim 1 wherein the aligning of the stored first and second portions of data is further accomplished by shifting at least one of said stored first and second portions of data an integral number of pixels.

3. A method as recited in claim 2 wherein the detection of misalignment of the stored first and second portions of data is accomplished using a sum of squared difference algorithm to dynamically determine any registration error therebetween.

4. A method as recited in claim 3 wherein the detection of misalignment of the stored first and second portions of data is accomplished by computing the sum of squared differences of the compared subportions of data shifted integral pixel amount relative to one another, finding the shift which minimizes the sum of squared differences, and interpolating between integer shifts to find the optimum subpixel shift.

5. A method as recited in claim 3 wherein said sum of squared difference algorithm includes the comparison of first data from a particular array of pixels in said first portion of data to second data from each of a plurality of iterations of a corresponding array of pixels from said second portion of data, each iteration being shifted a selected predetermined increment in orthogonal X and-/or Y directions relative to said corresponding array of pixels to perform a sum of squared difference operation between said first data and each of said second data so as to dynamically determined which shifted position of said second data has the best correlations to said first data.

6. A method as recited in claim 5 wherein said particular array is an nxm array of pixel data from said first portion of data, and said plurality of iterations are arrays of shifted data derived from a corresponding nxm array of pixel data from said second portion of data, each said shifted array being shifted a different increment relative to said corresponding nxm array, and wherein the minimum value array the sum of squared differences computed from said particular array and said nxm shifted arrays indicates the X and Y shifts required for alignment of said first and second portions of data, said X and Y shifts being used to align the stored portions of data.

7. A method as recited in claim 6, wherein n equals 5, m equals 480, and wherein said different increments are selected from the series −7, −6, −5 ... 0 ... 5, 6, 7.

8. A method as recited in claim 7, wherein the comparing of corresponding subportions of said aligned first and second portions of data is accomplished by correlating data corresponding to a particular pxp array of pixel data from said aligned first portion of data to a plurality of pxp arrays of shifted data derived from a corresponding pxp array of pixel data from said aligned second portion of data, each said shifted pxp array being shifted a different subpixel increment relative to said corresponding pxp array, and developing corresponding correlation values, and then comparing said correlation values to a predetermined threshold to detect the presence of a defect.

9. A method as recited in claim 8, wherein p equals 5, and wherein said different subpixel increments are $m \times \frac{1}{3}$ pixel where m is selected from the series −2, −1, 0, 1, 2.

10. A method as recited in claim 7, wherein the comparing of corresponding subportions of said aligned first and second portions of data is accomplished by an area subtraction algorithm in which pixel data representing a particular q×q array of pixel data from said aligned first portion of data is added together and subtracted from sum of pixel data from a shifted q×q array of pixel data from said second stored portion of data shifted a subpixel increment relative to a q×q array corresponding to said particular q×q array, and wherein the result of such subtraction is compared to a threshold, such that if said result exceeds said threshold, the presence of an error is indicated.

11. A method as recited in claim 10, wherein q equals 2, and wherein said subpixel increment is r×1/16 pixel where r is selected from the series 0, 1, 2, ... 15.

12. A method as recited in claim 1 wherein the detection of misalignment of the stored first and second portions of data is accomplished by computing the maximum of the cross correlation function and then performing a commensurate shift of at least one of said stored first and second portions of data to achieve alignment.

13. A method as recited in claim 1, wherein the stored first and second portions of data are aligned by shifting one portion with respect to the other in integral pixel shifts accomplished by displacing addresses in memory, shifts of less than one pixel being accomplished by subpixel interpolation.

14. A method as recited in claim 13 wherein the type of interpolation used is selected from the group consisting of;
  (a) linear interpolation,
  (b) s-curve interpolation,
  (c) fitting a polynomial or other general function to several pixels, and
  (d) sin x/x interpolation or an approximation thereof.

15. A method as recited in claim 1 wherein the comparing of corresponding subportions of said aligned first and second portions of data is accomplished by correlating of data corresponding to a particular pxp array of pixel data from said aligned first portion of data to a plurality of pxp arrays of shifted data derived from a corresponding pxp array of pixel data from said aligned second portion of data, each said shifted pxp array being shifted a different subpixel increment relative to said corresponding pxp array, and developing corresponding correlation values, and then comparing said correlating values to a predetermined threshold to detect the presence of a defect.

16. A method as recited in claim 15, wherein p equals 5, and wherein said different subpixel increments are $m \times 1/3$ pixel where m is selected from the series −2, −1, 0, 1, 2.

17. A method as recited in claim 1, wherein the comparing of corresponding subportions of said aligned first and second portions of data is accomplished by an area subtraction algorithm in which pixel data representing a particular qxq array of pixel data from said aligned first portion of data is added together and subtracted from sum of pixel data from a corresponding qxq array of pixel data from said second stored portion of data shifted a subpixel increment relative to said corresponding qxq array, and wherein the result of such subtraction is compared to a threshold, such that if said result exceeds said threshold, the presence of an error is indicated.

18. A method as recited in claim 17, wherein q equals 2, and wherein said different subpixel increments are $m \times 1/16$ pixel where r is selected from the series 0, 1, 2, ... 15.

19. A method as recited in claim 1 and further comprising the step of:
  performing interpolations in orthogonal X and Y directions on said first stream of data, before said portions thereof are stored in memory, to correct geometrical distortions of the image data, and
  delaying said second stream of data for a period commensurate with the time required to correct said first stream of data.

20. A method as recited in claim 19, wherein said interpolations in said X and Y directions are made in response to adjustment parameters previously determined during a calibration operation.

21. A method as recited in claim 20, wherein said first stream of data is first interpolated in the X direction to correct for rotation of a sensor array and the results thereof are then interpolated in the Y direction to correct for said magnification and distortion errors.

22. A method as recited in claim 20, wherein said first stream of data is first interpolated in the Y direction to correct for magnification and distortion errors and the results thereof are then interpolated in the X direction to correct for rotation of a sensor array.

23. A method as recited in claim 1, wherein the said first and second surface areas of an object are inspected using a pair of electro-optical systems and said first and second streams of data respectively correspond thereto, and further comprising the steps of:
  developing orthogonal X and Y interpolation data corresponding to the detection characteristics of said pair of electro-optical systems, where any combination of X and Y interpolation data uniquely defines joint interrelational detection characteristics of the electro-optical systems as they relate to optical and mechanical distortion of detected pixel data passing through said electro-optical systems;
  using said X interpolation data to perform a first dynamic interpolation of data in said first stream of data before said portions thereof are stored in memory;
  using said Y interpolation data to perform a second dynamic interpolation of the X interpolated data in said first stream before said portions thereof are stored in memory; and delaying said second stream of data for a period of time such that the delayed second stream of data is time coincident with the X and Y interpolated first stream of data.

24. A method as recited in claim 1 and further comprising the steps of:
performing a critical dimension correction on said first and second streams of data using an interpolation scheme which adjusts the data in at least one of said data streams so that the dimensions of object features represented in the two streams are substantially equal.

25. A method as recited in claim 24, wherein said critical dimension correction is performed by measuring the percentage of corresponding large areas of image data covered by said object features in said first and second data streams, and measuring the respective perimeters of such object features, and then dividing the measured value of said area by the measured value of said perimeters to obtain a measure of the dimensional change required to cause corresponding data in both streams to match, and adjusting the data in at least one of said data streams to effect said match.

26. A method as recited in claim 25, wherein said adjustments are made by digitally remapping the pixel grey level data up or down in magnitude to dynamically cancel the effects of variations in linewidths due to process variations.

27. A method as recited in claim 26, wherein said digital remapping is accomplished using an S-curve interpolation algorithm in which the magnitude of said pixel grey level data is adjusted in a predetermined manner depending on where the corresponding pixel falls on an edge thereby effectively increasing or decreasing the linewidth.

28. A method as recited in claim 1 wherein the said inspecting step is accomplished using a pair of optical systems which generate said first and second streams of data, and wherein said first and second streams of data relate to corresponding surface areas of objects having supposedly identical features represented by data of a first signal level, background represented by data of a second signal level, and feature edges represented by data having signal levels in between said first level and said second level, comprising:
mapping the edge data of said first data stream;
mapping the edge data of said second data stream;
detecting the positional relationship of corresponding edge data in said first and second data streams; and
using the detected positional relationship to remap the edge data of at least one of said data streams so that edge data of the remapped data stream is more nearly positionally coincident with the corresponding edge data of the other data stream.

29. An Apparatus for inspecting objects such as photomasks and the like for defects, comprising:
means for inspecting a selected surface area of an object and for generating a first stream of data having signal values representing the image content of each pixel thereof;
means for generating a second stream of data having signal values representing the image content of each pixel of said second stream of data;
memory means for storing corresponding portions of said first and second streams of data;
detector means for detecting with resolution to a fraction of a pixel any misalignment between the stored first and second portions of data;
alignment means using subpixel interpolation to correct any detected misalignment in the stored first and second portions of data; and
detector means for comparing corresponding subportions of the aligned first and second portions of data to detect any difference therebetween, and upon detecting such difference, for indicating the presence of a defect at a particular pixel location on the inspected object.

30. Apparatus as recited in claim 29 wherein said alignment means includes logic circuitry for implementing a sum of squared difference algorithm to dynamically determine any registration error between the stored firs and second subportions of data.

31. Apparatus as recited in claim 30 wherein said logic circuitry includes
means for generating sum of squared difference data relating to a particular nxm array of pixel data from said first portion of data and a corresponding nxm array of pixel data from said second portion of data, and for further generating sum of squared difference data relating to said particular nxm array and a plurality of shifted iterations of said corresponding nxm array, each said shifted nxm array being shifted a pixel integer increment in X and/or Y directions relative to said corresponding nxm array, and
wherein said alignment means further includes processor means for using said sum of squared difference data to correct said detected misalignment.

32. Apparatus as recited in claim 31 wherein said processor means includes means for determining the pixel shift which minimizes the sum of squared differences, and means for interpolating between integer shifts to find the optimum subpixel shifts.

33. Apparatus as recited in claim 32 wherein said alignment means causes the stored first and second portions of data to be aligned by shifting one portion with respect to the other an amount determined by said alignment means, integral pixel shifts being accomplished by displacing addresses in memory means, and shifts of less than one pixel in X and Y being accomplished by interpolation.

34. Apparatus as recited in claim 33 wherein said alignment means includes interpolation means for implementing interpolation of a type selected from the group including;
(a) linear interpolation,
(b) s-curve interpolation,
(c) fitting a polynomial or other general function to several pixels, and
(d) sin x/x interpolation or an approximation thereof.

35. Apparatus as recited in claim 31 wherein n equals 5, m=480 and wherein said integer shifts are selected from the series $-7, -6, -5 \ldots 0 \ldots 5, 6, 7$.

36. Apparatus as recited in claim 31, wherein said detector means includes
means for generating pixel data corresponding to a particular pxp array of said first portion of data and a corresponding pxp array of pixel data from second portion of data, and for further generating sum of squared difference data relating to said particular pxp array and a plurality of shifted iterations of said corresponding pxp array, each said shifted pxp array being shifted a pixel integer increment in X and/or Y directions relative to said corresponding p x p array, and means for comparing said sum of squared difference data to a selected threshold value and for indicating a defect if all of said sum of squared difference data exceeds said threshold.

37. Apparatus as recited in claim 36, wherein p equals 5, and wherein said different subpixel increments are $m \times \frac{1}{3}$ pixel where m is selected from the series $-2, -1, 0, 1, 2$.

38. Apparatus as recited in claim 31 wherein said detector means includes
   logic circuitry for implementing an area subtraction algorithm in which pixel data representing a particular $q \times q$ array of pixel data from said aligned first portion of data is added together and subtracted from sum of pixel data from a shifted $q \times q$ array of pixel data from said second stored portion of data shifted a subpixel increment relative to a $q \times q$ array corresponding to said particular $q \times q$ array and
   means for comparing the result of such subtraction to a threshold, such that if said result exceeds said threshold, the presence of a defect is indicated.

39. Apparatus as recited in claim 38, wherein q equals 2, and wherein said subpixel increment is $r \times 1/16$ pixel where r is selected from the series $0, 1, 2, \ldots 15$.

40. Apparatus as recited in claim 29, wherein said detector means includes
   means for generating pixel data corresponding to a particular $p \times p$ array of said first portion of data and a corresponding $p \times p$ array of pixel data from said second portion of data, and for further generating sum of squared difference data relating to said particular $p \times p$ array and a plurality of shifted iterations of said corresponding $p \times p$ array, each said shifted $p \times p$ array being shifted an integer pixel increment in X and/or Y directions relative to aid corresponding $p \times p$ array, and
   means for comparing said sum of squared difference data to a selected threshold value and for indicating a defect if all of said sum of squared difference data exceed said threshold.

41. Apparatus as recited in claim 29 wherein said detector means includes
   logic circuitry for implementing an area subtraction algorithm in which pixel data representing a particular $q \times q$ array of pixel data from said aligned first portion of data is added together and subtracted from sum of pixel data from a shifted $q \times q$ array of pixel data from said second stored portion of data shifted a subpixel increment relative to a $q \times q$ array corresponding to said particular $q \times q$ array and
   means for comparing the result of such subtraction to a threshold, such that if said result exceeds said threshold, the presence of an error is indicated.

42. Apparatus as recited in claim 29 wherein at least said means for inspecting includes an optical system and associated photodetector means for generating said first stream of data, and further comprising:
   means for performing interpolations in orthogonal X and Y directions on said first stream of data before said portions thereof are stored in said memory means, said interpolations being operative to correct for opto-mechanical distortion of said data; and
   means for delaying said second stream of data for a period commensurate with the time required to correct said first stream of data.

43. Apparatus as recited in claim 29 wherein said means for generating the second stream of data having signal values representing the image content of each pixel thereof is a data processing system designed to produce from a database ideal image data against which the first stream of data can be compared.

44. Apparatus as recited in claim 29 wherein at least one of said means for inspecting and said means for generating includes an optical system and associated photodetection means for generating said streams of data, and further comprising:
   means for developing orthogonal X and Y interpolation data corresponding to the detection characteristics of said optical system, where any combination of X and Y interpolation data uniquely defines the optical characteristics of the optical system as they relate to optical and mechanical distortion of detected pixel data obtained from corresponding pixel areas of said object;
   means for using said X interpolation data to perform a first dynamic interpolation of data in said first stream of data before said portion thereof is stored in said memory means;
   means for using said Y interpolation data to perform a second dynamic interpolation of the X interpolated data in said first stream before said portion thereof is stored in said memory means; and
   means for delaying said second stream of data for a period of time such that the delayed second stream of data is time coincident with the X and Y interpolated first stream of data.

45. Apparatus as recited in claim 29 and further comprising:
   means for performing a critical dimension correction on said first and second streams of data by adjusting the data in at least one of said data streams so that the dimensions of object features represented in the two streams are substantially equal.

46. Apparatus as recited in claim 45, wherein said means for performing a critical dimension correction includes means for measuring the percentage of corresponding large areas of image data covered by said object features in said first and second data streams, and for measuring the respective perimeteres of such object features, and then dividing the measured value of said area by the measured values of said perimeters to obtain a measure of the dimensional change required to cause data in both streams to match, and means for adjusting the data in at least one of said data streams to effect said match.

47. Apparatus as recited in claim 46 wherein said means for adjusting includes means for digitally remapping up or down in magnitude the pixel grey level data representing said edges to dynamically cancel the effects of variations in linewidths due to process variations.

48. Apparatus as recited in claim 47 wherein said means for remapping uses an S-curve interpolation algorithm in which the magnitude of said pixel grey level data is adjusted in a predetermined manner depending on where a particular pixel falls on an edge, thereby effectively increasing or decreasing the linewidth.

49. Apparatus as recited in claim 46 wherein the detected positional relationship is used to remap the corresponding edge data of each data stream so that each is more nearly positionally coincident with the remapped edge data of the other.

50. Apparatus as recited in claim 49 wherein the remapping operation is accomplished by means of an S-curve algorithm in which the signal level of edge data corresponding to each pixel of an edge transition is adjusted in magnitude by a predetermined increment depending on the position of the pixel in the edge transition and the direction of the remapping operation.

51. A method of detecting defects in objects such as photomasks, reticles, wafers, printed circuit boards, and the like, comprising the steps of:

inspecting a selected surface area of an object and generating a first stream of data having signal values representing the image content of each pixel thereof;

generating a second stream of data having signal values representing the image content of each pixel of said second stream of data;

storing corresponding portions of the first and second streams of data in memory;

detecting with a resolution to an integer pixel any misalignment between the stored portions of said first and second streams of data;

aligning the stored first and second portions of data to the closest integer pixel to correct any detected misalignment therebetween; and comparing corresponding subportions of the stored and aligned first and second portions of data to detect differences therebetween by correlating data corresponding to a particular pxp array of pixel data from said aligned first portion of data to a plurality of p×p arrays of shifted data derived from a corresponding p×p array of pixel data from said aligned second portion of data, each said shifted pxp array being shifted a different subpixel increment relative to said corresponding p×p array and developing corresponding correlation values, and then comparing said correlation values to a predetermined threshold to detect the presence of a defect.

52. A method of detecting defects in objects such as photomasks, reticles, wafers, printed circuit boards, and the like, comprising the steps of:

using a first electro-optical system to inspect a first selected surface area of an object and to generate a first stream of data having signals values representing the image content of each pixel thereof;

using a second electro-optical system to inspect a second surface area of said object and to generate a second stream of data having signal values representing the image content of each pixel of said second stream of data;

storing corresponding portions of the first and second streams of data in memory;

detecting with a resolution to a fraction of a pixel any misalignment between the stored portions of said first and second streams of data;

aligning the stored first and second portions of data using subpixel interpolation to correct any detected misalignment therebetween; and comparing corresponding subportions of the stored and aligned first and second portions of data to detect differences therebetween by correlating data corresponding to a particular p×p array of pixel data from said aligned first portion of data to a plurality of p×p arrays of shifted data derived from a corresponding p×p array of pixel data from said aligned second portion of data, each said shifted p×p array being shifted a different subpixel increment relative to said corresponding p×p array and developing corresponding correlation values, and then comparing said correlation values to a predetermined threshold to detect the presence of a defect.

* * * * *

REEXAMINATION CERTIFICATE (3645th)

United States Patent [19]

Specht et al.

[11] B1 4,805,123
[45] Certificate Issued Oct. 13, 1998

[54] AUTOMATIC PHOTOMASK AND RETICLE INSPECTION METHOD AND APPARATUS INCLUDING IMPROVED DEFECT DETECTOR AND ALIGNMENT SUBSYSTEMS

[75] Inventors: Donald F. Specht, Los Altos; Tim S. Wihl, San Jose; Scott A. Young, Scotts Valley; James J. Hager, Jr., San Jose; Matthew B. Lutzker, Menlo Park, all of Calif.

[73] Assignee: KLA Instruments Corporation, Santa Clara, Calif.

Reexamination Request:
No. 90/002,732, Jun. 1, 1992

Reexamination Certificate for:
Patent No.: 4,805,123
Issued: Feb. 14, 1989
Appl. No.: 885,197
Filed: Jul. 14, 1986

[51] Int. Cl.$^6$ .............................. G06K 9/68; G06K 9/38
[52] U.S. Cl. .................... 382/144; 382/151; 348/126; 356/394
[58] Field of Search .................... 364/559; 356/394; 382/8, 34, 48; 358/105

[56] References Cited

U.S. PATENT DOCUMENTS

| | | | |
|---|---|---|---|
| 3,573,789 | 4/1971 | Sharp | 347/728 |
| 4,110,737 | 8/1978 | Fahey | 382/44 |
| 4,129,860 | 12/1978 | Yonezawa et al. | 340/728 |
| 4,136,332 | 1/1979 | Kadota et al. | 382/34 |
| 4,153,897 | 5/1979 | Yasuda et al. | 382/34 |
| 4,200,861 | 4/1980 | Hubach et al. | 382/48 |
| 4,437,121 | 3/1984 | Taylor et al. | 382/46 |
| 4,441,205 | 4/1984 | Berhin et al. | 382/34 |
| 4,448,532 | 5/1984 | Joseph et al. | 356/394 |
| 4,579,455 | 4/1986 | Levy et al. | 356/394 |
| 4,611,232 | 9/1986 | Searby | 358/160 |
| 4,614,430 | 9/1986 | Hara et al. | 382/8 |
| 4,631,750 | 12/1986 | Gabriel et al. | 382/44 |
| 4,644,584 | 2/1987 | Nagashima et al. | 382/48 |
| 4,651,341 | 3/1987 | Nakashima et al. | 382/34 |
| 4,669,123 | 5/1987 | Kobayashi et al. | 382/8 |
| 4,680,630 | 7/1987 | Field | 382/46 |
| 4,693,608 | 9/1987 | Kitagawa et al. | 356/394 |
| 4,701,859 | 10/1987 | Matsuyama et al. | 382/8 X |

FOREIGN PATENT DOCUMENTS 3340705  5/1984  Germany.

OTHER PUBLICATIONS

*Digital Picture Processing*, Second Edition, Rosenfeld, et al., Chapter 9, published 1982.

*Primary Examiner*—Michael Zanelli

[57] ABSTRACT

A photomask and reticle inspection method and apparatus wherein a selected surface area of an object is inspected and a first stream of data having signal values representing the image content of each pixel thereof is generated, a second stream of data having signal values representing the intended image content of each pixel of the first stream of data is generated, corresponding portions of the first and second streams of data are stored in memory, any misalignment between the stored portions of the first and second streams of data is detected, the misaligned first and second portions of data are then aligned using shifts of an integral number of pixels and/or subpixel interpolation to correct the detected misalignment therebetween, corresponding subportions of the stored and aligned first and second portions of data are then compared to detect difference therebetween, and upon detecting a difference exceeding a predetermined threshold, the presence of a defect at a particular pixel location on the inspected object is indicated.

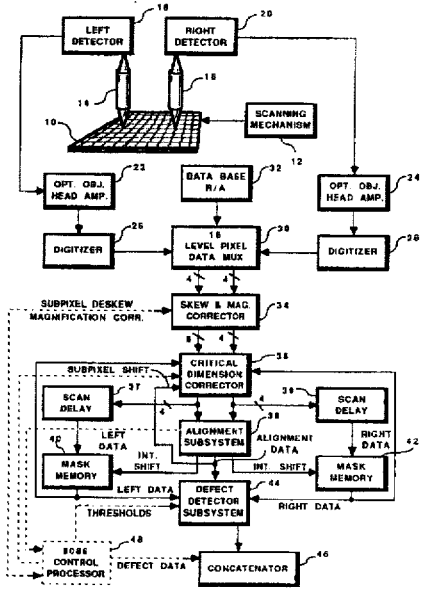

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–52 is confirmed.

* * * * *